(12) United States Patent
Abad et al.

(10) Patent No.: US 7,655,756 B2
(45) Date of Patent: Feb. 2, 2010

(54) CRYSTALLIZED STRUCTURE OF ESTROGEN RELATED RECEPTOR GAMMA IN COMPLEX WITH BISPHENOL A

(75) Inventors: Marta C. Abad, Downingtown, PA (US); Dionisios Rentzeperis, Downingtown, PA (US); John O'Neill, Downingtown, PA (US); Hossein B. Askari, Exton, PA (US); Cynthia M. Milligan, Exton, PA (US); Frank A. Lewandowski, Exton, PA (US)

(73) Assignee: Johnson & Johnson Pharmaceutical Research & Development, LLC, New Brunswick, NJ (US)

( * ) Notice: Subject to any disclaimer, the term of this patent is extended or adjusted under 35 U.S.C. 154(b) by 0 days.

(21) Appl. No.: 11/442,004

(22) Filed: May 26, 2006

(65) Prior Publication Data

US 2006/0270836 A1     Nov. 30, 2006

Related U.S. Application Data

(60) Provisional application No. 60/685,364, filed on May 27, 2005.

(51) Int. Cl.
*C07K 14/00* (2006.01)
*A61K 38/16* (2006.01)
*C08H 1/00* (2006.01)

(52) U.S. Cl. .................. 530/350; 530/358; 530/402

(58) Field of Classification Search .............. None
See application file for complete search history.

(56) References Cited

U.S. PATENT DOCUMENTS

| | | | |
|---|---|---|---|
| 6,069,239 | A | 5/2000 | Mathias |
| 6,359,116 | B1 | 3/2002 | Mathias |
| 2004/0009558 | A1 | 1/2004 | Moras et al. |
| 2005/0074765 | A1 | 4/2005 | Blanchard et al. |

FOREIGN PATENT DOCUMENTS

| WO | WO 03/034028 A | 4/2003 |
|---|---|---|
| WO | WO 03/064468 A | 8/2003 |

OTHER PUBLICATIONS

Branden et al., "Introduction to Protein Structure Second Edition", Garland Publishing Inc., New York, 1999.*
Drenth, "Principles of X-ray Crystallography," Springer, New York, 1995.*
Kierzek et al., Biophys Chem 91:1-20, 2001.*
Suzuki et al., Neuroscience, 117, p. 639-644, 2002.*
Lorke et al., Molecular Brain Research, 77, p. 277-280, 2000.*
Takayanagi et al., Toxicology Letters, 167, p. 95-105, 2006.*
Giege et al. Crystallogenesis of Biological Macromolecules: Facts and Perspectives. Acta Cryst., 1994, D50: 339-350.*
Hong Heng et al: "Hormone-Independent Transcriptional Activation and Coactivator Binding by Novel Orphan Nuclear Receptor ERR3", Journal of Biological Chemistry, vol. 274, No. 32, Aug. 6, 1999, pp. 22618-22626, ISSN: 0021-9258.
Greschik et al., "Structural basis for the deactivation of the estrogen-related receptor γ by diethylstilbestrol or 4-hydroxytamoxifen and determinants of selectivity", J. Biol. Chem., vol. 279, No. 32, pp. 33639-33646 (2004).
Greschik et al., "Structural and functional evidence for ligand-independent transcriptional activation by the estrogen-related receptor 3", Mol. Cell, vol. 9, No. 2,: pp. 303-313 2002).
Willy et al., "Unique requirements for retinoid-dependent transcriptional activation by the orphan receptor LXR", Genes Dev., vol. 11, No. 3, pp. 289-298 (1997).
Willy et al., "Regulation of PPARγ coactivator 1α (PGC-1α) signaling by an estrogen-related receptor α (ERRα) ligand", Proc. Natl. Acad. Sci. USA, vol. 101, No. 24, pp. 8912-8917 (2004).
Zuercher, et al., "Identification and structure-activity relationship of phenolic acyl hydrazones as selective agonists for the estrogen-related orphan nuclear receptors ERRβ and ERRγ", J. Med. Chem., vol. 48, No. 9, pp. 3107-3109 (2005).

* cited by examiner

*Primary Examiner*—Nashaat T Nashed
*Assistant Examiner*—Jae W Lee
(74) *Attorney, Agent, or Firm*—Andrea Jo Kamage

(57) ABSTRACT

A method for the identification of novel compounds that interact and stabilize the ligand binding domain of estrogen-related receptor gamma (ERRγ), a methodology for producing diffraction quality crystal structures in the presence of antagonist and agonist ligands, including Bisphenol A, and the identification of novel biologically-active compounds that have an effect on the transcriptional-activating activity of ERRγ are disclosed.

2 Claims, 10 Drawing Sheets

CRYSTALLIZED STRUCTURE OF ESTROGEN RELATED RECEPTOR GAMMA IN COMPLEX WITH BISPHENOL A

CROSS-REFERENCE TO RELATED APPLICATIONS

This application claims priority to Application No. 60/685,364 filed on May 27, 2005.

FIELD OF THE INVENTION

The present invention includes a method for the identification of novel compounds that interact and stabilize the ligand binding domain of ERRγ, a methodology for producing diffraction quality crystal structures in the presence of antagonist and agonist ligands and the identification of novel biologically-active compounds that have an effect on the transcriptional activity of ERRγ.

BACKGROUND OF THE INVENTION

Nuclear hormone receptors (NHRs) play key roles in development, homeostasis, and disease (Kliewer, Lehmann et al. 1999; Chawla, Repa et al. 2001; Olefsky 2001). Targeted gene deletion of these receptors in mice has proven their association with different diseases including atherosclerosis, cancer, diabetes, and lipid disorders (Horard and Vanacker 2003; Smith and Muscat 2005; Glass 2006). These findings have opened new strategies for treatment of these diseases, and implicate orphan receptors as important targets for drug discovery. Nuclear receptors (NR) act as ligand-inducible transcription factors that are regulated by binding to small lipophilic molecules such as steroid and thyroid hormones or the active forms of vitamin A (retinoids) and vitamin D (Moras and Gronemeyer 1998; Escriva, Delaunay et al. 2000; Aranda and Pascual 2001; Kumar, Johnson et al. 2004). These molecules play an important role in the embryonic development, growth, differentiation, metabolism, reproduction, homeostasis and morphogenesis of higher organisms and humans. Several members of the nuclear receptor family for which ligands have not been identified are classified as orphan receptors (Blumberg and Evans 1998; Giguere 1999).

The estrogen related receptors (ERRs) were the first orphan NR to be discovered and to date three members have been identified (ERRα, ERRβ and ERRγ). The ERR subfamily is closely related to the estrogen receptors ERα and ERβ. ERRα and ERRβ were first isolated by a low stringency hybridization screen (Giguere, Yang et al. 1988) followed later with the discovery of ERRγ (Hong, Yang et al. 1999). Though sharing structural homology with the estrogen receptors, these receptors do not bind estrogens. Unlike classical estrogen receptors that are ligand activated NR, the ERR's show varying levels of constitutive activity that appears to be tissue selective (Kraus, Ariazi et al. 2002; Horard and Vanacker 2003). The ERRs and ERs share sequence similarity with the highest homology observed in their DNA binding domains. They interact with classical DNA estrogen response elements and half sites (Johnston, Liu et al. 1997; Vanacker, Pettersson et al. 1999). Recent biochemical evidence has shown that the ERRs and ERs share co-regulatory proteins and can functionally interfere with estrogen responsive genes in the breast and bone including pS2, lactoferin, aromatase and osteopontin (Hong, Yang et al. 1999; Vanacker, Pettersson et al. 1999; Zhang and Teng 2000; Giguere 2002; Kraus, Ariazi et al. 2002). ERR's in addition to synergizing or competing with estrogen responsive genes have also been implicated in maintaining energy homeostasis (Kamei, Ohizumi et al. 2003). A recently described ERRα knock-out has reduced adiposity and is resistant to weight gain within 3-5 weeks after feeding a high fat diet (Luo, Sladek et al. 2003). Food consumption and energy expenditure were unaltered. Gene expression profiling of the small intestine and adipose tissues of these knock-out animals show alterations in expression levels of genes involved in fatty acid metabolism and absorption (Carrier, Deblois et al. 2004). This is consistent with the expression profile of ERRα that is predominately found in tissues and has increased capacity for fatty acid oxidation, storage and absorption (Sladek, Bader et al. 1997). The constitutive activity of ERRα is robustly stimulated by PGC-1, a co-activator that enhances fatty acid oxidation, oxidative phosphorylation and induces mitochondrial biogenesis (Schreiber, Emter et al. 2004). Small molecule antagonist against ERRα antagonized these ERRα:PGC-1 mediated responses in in vitro cellular assays but did not return them back to basal levels (Mootha, Handschin et al. 2004). These responses appear to be dependent on the presence of PPAR's and other PGC-1 transcription factor partners. Therefore ERRα augments or attenuates PPAR and PGC-1 responsive genes to external stimuli (Wende, Huss et al. 2005). ERRγ is highly expressed in metabolic active tissues during fetal development such as skeletal muscle, adipose and heart in a similar manner to ERRα (Heard, Norby et al. 2000). In the adult highest expression levels are observed in the heart, brain, kidney and pancreas (Hong, Yang et al. 1999). Its basal transcriptional activity is strongly stimulated in the presence of the PGC-1 family of transcription factors but little is known about the biological consequence of this interaction (Kamei, Ohizumi et al. 2003). In the ERRα knock-out no compensatory changes have been reported on the mRNA levels for ERRγ with the exception of in the heart where a ~2-fold increase was shown (Huss, Torra et al. 2004). This change was correlated with an equal change to PGC-1 levels, but the extent of each PGC-1 isoform in mediating biological responses still needs to be determined. ERRγ is positively correlated with ERα positive breast cancers (Ariazi, Clark et al. 2002) and is associated with a positive prognostic outcome for anti-estrogen therapies. The later might be due that 4OHT is a potent ligand for ERRγ (Coward, Lee et al. 2001).

One of the rate limiting steps in defining biological function for orphan NR is the discovery of interacting ligands that would pharmacologically modulate its biological activity. New screening technologies have been developed for the discovery of ligands for the orphan NHR, and have assisted in the identification of ligands that can be used as tools for elucidating the biology of these receptors (Shiau, Coward et al. 2001; Rosen, Marschke et al. 2003). This approach is referred to as "reverse endocrinology" (Heyman, Mangelsdorf et al. 1992). Although a high-risk endeavor, the ERR NR are highly druggable as several reports have attested to in recent years. Pharmacological modulation of ERRα by the small molecule antagonist XCT790 has elucidated the role of ERRα in the regulation of oxidative phosphorylation genes (Busch, Stevens et al. 2004; Willy, Murray et al. 2004). X-ray crystallography studies of 4OHT and di-ethylstilbestrol (DES) showed that ERRγ and ERRγ are antagonists and the determined co-crystal structure of ERRγ provided the molecular basis of the observed antagonism (Coward, Lee et al. 2001; Greschik, Flaig et al. 2004). Phenolic acyl hydrazones have been described as ERRγ agonists although no details were given on the molecular basis for the observed agonist response (Zuercher, Gaillard et al. 2005). The present invention is directed to ligands that stabilize the ligand binding domain for all three members of the ERR family as determined using ThermoFluor® as a high throughput screening (HTS) platform (Pantoliano, Petrella et al. 2001). ThermoFluor® exploits the well characterized phenomenon of ligand induced stabilization of macromolecules (Rentzeperis, Marky et al. 1995). The technology provides competitive advantages over existing technologies since it does not require a functional response and can detect low affinity ligands (Grasberger, Lu et al. 2005; Matulis, Kranz et al. 2005).

Compounds that associate and stabilize the ligand binding domain of ERRγ have been identified. Affinities for these ligands were measured by isothermal methods and their functional response was determined by a co-activator recruitment assay. Two of the identified phenol containing ligands, BPA and $ClCH_3Ph$, associate with potencies of 70 and 380 nM respectively, and compete for 4OHT binding, a reported antagonist of ERRγ. The structures for these two compounds were determined to resolutions of 2.1 and 2.3 Å, respectively. Superimposition of the structures with the reported constitutively active apo-form of the receptor showed no changes in the overall conformation of the receptor consistent with the ligands being functionally silent.

The Estrogen-Related Receptor 3 (ERR3), also termed Estrogen-Related Receptor gamma (ERRγ), belongs to the family of estrogen-related receptors. Although their biological function is not well understood, ERRs (ERRα, ERRβ and ERRγ) are regarded as constitutively active and no natural ligands that will regulate their function have yet been identified. Estrogen-related receptors themselves belong to the family of Nuclear Receptors (NRs). Orphan members of the nuclear receptor (NR) superfamily were initially identified by their high homology with the steroid or retinoid receptors and are hypothesized to be ligand-regulated despite the lack of a known ligand (Willy et al., 1997; Giguere, 1999)).

NRs play an important role in differentiation, development and metabolism. Their cognate ligands and relevant accessory proteins regulate highly specific biological activities. Knowledge of the ligands, accessory proteins and genes they regulate can provide new drug targets for the treatment of diseases such as diabetes, obesity, osteoporosis, heart disease and cancer.

U.S. Pat. Nos. 6,359,116 and 6,069,239 disclose the full length protein sequence of ERR3.

U.S. Application No. 20050074765 discloses a method of identifying compounds that will be useful for treatment of ERRγ and ER-mediated diseases.

U.S. Application No. 20040009558 ("the '558 application") discloses a peptide fragment that mimicks, when fused to a polypeptide containing a DNA-binding domain, the ligand dependence of the transcriptional activity of ERRγ. The '558 application also discloses a method for selecting a compound that interacts with the Ligand Binding Pocket (LBP) of ERR3 using the relative structural coordinates according to Table 1 therein and a crystallized protein as defined therein.

Current approaches to validate the therapeutic utility of a target for the treatment of a disease rely on genomic data and annotating function by sequence analysis. Once a target is validated then chemical libraries can be selected or synthesized that are centered on known chemotypes for the particular function of the target and assayed with conventional methods. Conventional assay development is problematic for orphan targets since they rely on competitive displacement of a known ligand or rely on a functional response. With ThermoFluor®, assay development for an orphan protein is not problematic (Grasberger, Lu et al. 2005). Ligands that will interact with the protein will be identified because they will produce a positive stabilization of the protein. If the stabilizing ligand is a biochemical, then a putative function can be assigned to the orphan protein and a biochemical, functional or cell-based assay can be designed to elucidate the biology of the protein. In this invention we have demonstrated the utility of ThermoFluor® in identifying ligands that stabilize ERRγ, an orphan nuclear receptor, and used crystallography to define the molecular basis of the functionally silent response of BPA and $ClCH_3Ph$ in our cellular trans-activation and co-activator TR-FRET assays. The diversity of ligands that were found to interact with this receptor raises the possibility of the existence of a natural ligand that can regulate the activity of ERRγ. Stabilization of the receptor can result in changes of steady state levels that can impact protein levels, phosphorylation states, that can impact biological activity through cross-talk to other nuclear receptors (Kojo, Tajima et al. 2006), alter affinity for response elements (Barry and Giguere 2005) or specific co-regulator interactions (Barry, Laganiere et al. 2006). The methodology described in the identification of stabilizing ligands and the novel hydrogen bonds observed with the ligands and the ERRγ reported structures will assist in the design of selective ERRγ modulators.

There is a need to identify compounds which modulate ERRs in order to provide biologically active compounds that exert an effect on the transcriptional-activating activity of ERRs. Such molecules can modulate the response of the receptor or impact biological response of other transcription factors by competing for ancillary proteins and DNA response elements and can be useful for the treatment of metabolic and endocrine disorders.

SUMMARY OF THE INVENTION

For this purpose, the invention discloses a peptide fragment comprising the Ligand Binding Domain (LBD) of ERRγ in complex with Bisphenol A, and a complex of the ligand binding domain of ERRγ in complex with chloro-cresol.

The invention also provides for means for producing the peptide fragment/Bisphenol A complex and for producing the peptide fragment/chlorocresol complex.

According to the present invention, the peptide fragment above is used for the screening of compounds which have an effect on ERRγ activity.

Another object of the invention is the method of screening the ligand binding domain of ERRγ against compounds in ThermoFluor® and examples for identifying compounds that stabilize the receptor. The functional response of the compounds can be agonist or antagonist.

The invention is also directed to the LBD of ERRγ under the form of a crystallized molecule or a crystallized molecular complex of specified structural coordinates.

According to the invention, the crystallized molecule or molecular complex above is used to design or select compounds which have an effect on ERRγ activity.

DESCRIPTION OF THE FIGURES

FIG. 1 shows representative thermal denaturation curves of ERRγ in ThermoFluor®. ERRγ (4 µM protein in 25 mM HEPES pH 8.0, 100 mM NaCl, 1 mM EDTA, 25 µM ANS and 2% DMSO) melted with at a characteristic temperature of 49.6° C. in the absence of ligand (o). In the presence of ClCH3Ph (●), BPA (■) or 4OHT (▲) at 100 µM the protein stability increased from 4.0 to 5.7° C.

FIG. 2 shows TR-FRET assay in the presence of ClCH3Ph, BPA or 4OHT. For FRET measurements, the reaction was buffered in 25 mM Tris pH 8, 2.5 mM Hepes, 20 mM KCl, 1 mM DTT, and 0.05 mg/mL delipidated BSA. The final concentrations of reagents were 6 nM of ERRγ LBD, 6 nM GST-SRC-2 peptide, 30 nM α-GST Europium Cryptate and 7.5 nM α⁶His-XL665 (⁶His disclosed as SEQ ID NO: 1) (allophycocyanin) fluorophore. A) Competitive displacement curves of GST-SRC2 in the presence of increasing concentration of ligand. 4OHT antagonized the ERR-SRC2 complex with an apparent IC50 value of 11 nM. BPA and ClCh3PH were ineffective in antagonizing the receptor coactivator complex. B) TR-FRET assay ran in the presence of 100 nM 4OHT that effectively inhibits the formation of the ERRγ-SRC2 complex. Both BPA and ClCH3Ph allowed formation of the ERRγ-SRC2 complex by competitive displacement of 4OHT. Apparent EC50's obtained were 120 and 500 nM respectively.

FIG. 3 shows comparison between the LBPs of ERRγ-BPA (light gray) and the ERRγ-SRC peptide (medium gray) structures. E275 moves to make hydrogen bond interaction with the ligand. ERRγ-BPA's ligand is depicted in dark gray. Ligands and residues atoms are colored by element nitrogen (black), and oxygen (medium dark grey).

FIG. 4 shows comparison between the structures of LRRγ-BPA (light gray) and LRRγ-ClCH3Ph (medium gray). Ligands are depicted in dark gray for BPA and light medium gray for ClCH3Ph. Ligands and residues atoms are colored by element nitrogen (black), and oxygen (medium dark gray).

FIG. 5 shows final 2Fo-Fc electron density map of the different ligands. A) BPA contoured at 1.5 s. B) ClCH₃Ph contoured at 1.3 s and C) 4OHT contoured at 1.3 s.

FIG. 6.

FIG. 7 shows an overlay of the 4OHT ligands of two ERRγs and one ERα structures. Our ERRγ-4OHT structure is shown in light gray, Greischik's ERRγ-4OHT in dark gray and ERα-4OHT in medium gray.

FIG. 8 shows an overlay of the LBPs of ERα-4OHT over ERRγ-4OHT. The F435L mutation allows 4OHT to bind without disturbing H12 in ERα. ERRγ-4OHT residues shown in medium gray with ligand in light gray and ERα-4OHT residues in blue light medium gray and with ligand in dark gray. ERRγ numbering was use on the figure.

DETAILED DESCRIPTION OF THE INVENTION

Figure 1:
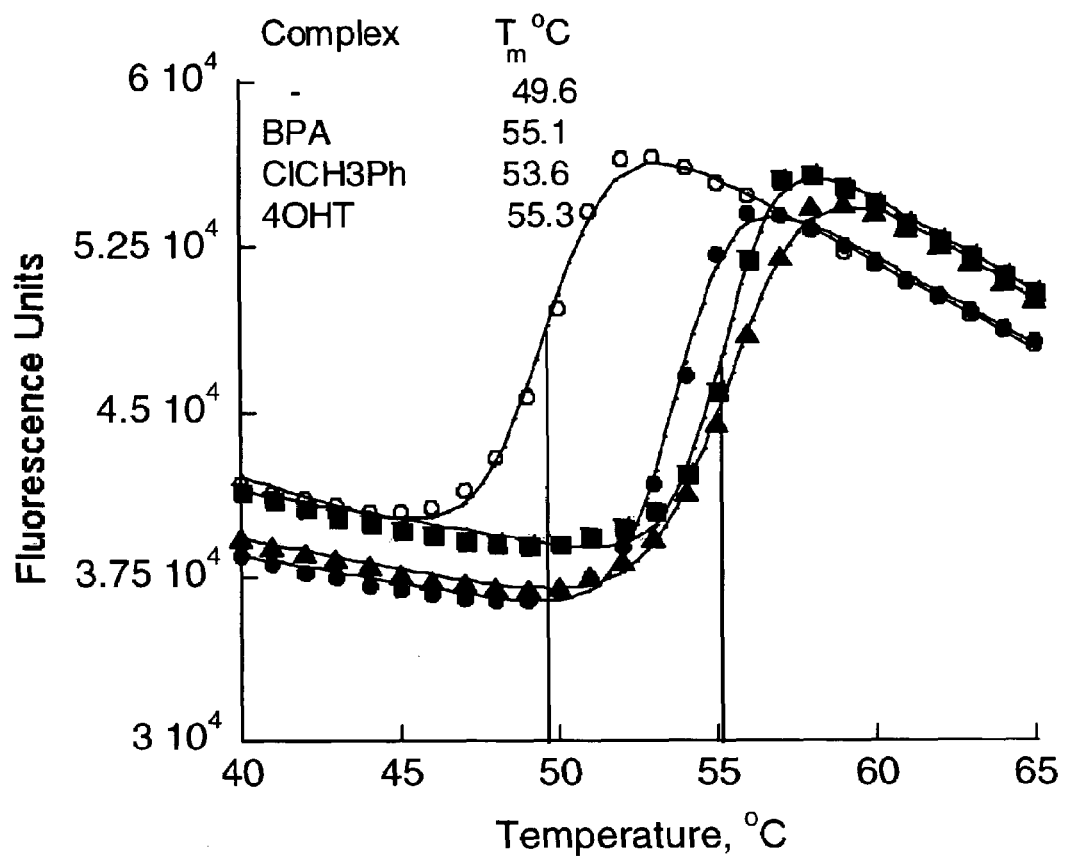
FIG. 1.

To date, the structure of ERRγ in the activated conformation in the presence of a small molecule ligand has not been shown. The present inventors have determined the structure of human ERRγ ligand binding domain (LBD) residues 235-456 in complex with three ligands identified by ThermoFluor® and confirmed by isothermal titration calorimetry. The structures of bisphenol A (BPA) and 4-chloro, 3-methyl phenol (ClCH3PH) were determined to a resolution of 2.1 and 2.3 Å, respectively, and the antagonist 4-hydroxytamoxifen (4OHT) was refined to 2.5 Å resolution. ERRγ's N346-OH interaction observed in the BPA structure is specific to ERRγ compared to the other ERs and ERRs (ERRα (Gly), ERRβ (Tyr), ERα (Phe) and ERβ (Phe)). This interaction has not been observed before. Previously determined structures include: ERRγ complexed with a steroid receptor coactivator-1 (SRC-1) peptide [Greschik, H., Wurtz, J.-M., Sanglier, S., Bourguet, W., Van Dorsselaer, A., Moras, D., Renaud, J.-P. Mol. Cell 9 pp. 303 (2002)], ERRγ in complex with diethylstillbestrol and the ERRγ-4OHT complex structure [Greschik, H., Flaig, R., Renaud, J. P., Moras, D. J. Biol. Chem. 279 pp. 33639 (2004)].

The structure of the ERRγ in complex with Bisphenol A (BPA) revealed the hydroxide groups of the ligand within hydrogen bond distance to residues N346, R316, E275 and the carbonyl of L309. A hydrogen bond between Y326 and N346 holds N346 in position to interact with BPA's second phenyl ring. ERRγ's asparagine at position 346 is not conserved among nuclear receptors (ERRα (Gly), ERRβ (Tyr), ERα (Phe) and ERβ (Phe)). This asparagine makes the N346-OH interaction specific to ERRγ, compared to the other ERs and ERRs. This interaction can be employed in efforts to achieve specificity over the other ERs and ERRs for the design of specific modulators, including agonist and antagonist ligands. In addition, the space group of the solved crystal is significantly different than those reported in the public databases for the ERRγ crystal structures.

EXAMPLE

A. Materials and Methods

A1. Cloning, Expression and Purification

Human ERRγ-ligand binding domain (LBD) (229-458) was subcloned in a pET28a vector (Novagen). The vector was in *E. coli* BL21(DE3) and cultured in Minimal media (M9) at 37° C. to an OD₅₉₅ 0.6-0.8, followed by induction at 15° C. with 0.4 mM IPTG for 20 hours. The next day, the culture was harvested and lysed in buffer A (Buffer A: 20 mM Tris-HCl, pH 7.5, 0.4 M NaCl and 5 mM Imidazole) using an Emulsiflex-C5 french press (Avestin). Lysates were spun at 40,000×g for 45 minutes to remove insoluble material. The clarified lysate was applied on a Ni-NTA column and eluted with a linear gradient of imidazole. The protein was further purified by applying the eluent on a Superdex 200 HR 10/30 column (Amersham Pharmacia Biotech) equilibrated with Buffer B (Buffer B: 20 mM Tris-HCl pH 7.5, 0.2M NaCl, 1 mM EDTA and 1 mM DTT). The aggregation state of the protein was confirmed by dynamic light scattering. Fractions were pulled and concentrated to 4 mg/ml and frozen in liquid nitrogen and stored at –80° C.

A2. ThermoFluor® Screen and Determination of Binding Constants

The ligand binding domain of ERRγ was screened against a library of known estrogen activators and a generic drug library using ThermoFluor®. ThermoFluor® is a miniaturized thermal shift assay, that has been developed for HTS applications; as a secondary assay for confirmation and characterization of hits; and as a functional assay to characterize orphan proteins. ThermoFluor® exploits the well-described phenomenon of ligand induced stabilization of macromolecules. Ligand binding energy adds directly to the ground state energy of a macromolecule and results in increased thermal stability. The degree of stabilization is proportional to the binding affinity of the ligand for the macromolecule.

Binding affinities of compounds were determined by screening against the ligand binding domain of ERR-γ using ThermoFluor® technology (U.S. Pat. No. 6,020,141, U.S. Pat. No. 6,036,920, and *Journal of Biomolecular Screening* 6 (6), 2002, pgs 429-440). Assay plates were prepared by dispensing 2 µL of a protein-dye solution and 2 µL of the test compound in a 384-well plate. The conditions used in the screen were: 0.1 mg/mL ERR-g, 25 µM ANS, 2% DMSO and the final concentration of test compound was 0-200 µM. Finally 1 µL of mineral oil was dispensed on top to prevent evaporation during the high throughput screen (HTS). ThermoFluor® is an HTS assay that measures protein unfolding based on fluorescence detection of the denatured form of the protein. The reporter for the protein unfolding event is the environmentally sensitive dye ANS that is incorporated in the screening buffer. During a typical experiment the 384-well plate is heated at a ramping rate of 1° C./min and the thermal unfolding of the protein is monitored at 1° C. intervals by measuring fluorescence changes detected through a CCD camera. Captured images are integrated and a melting curve is generated that relates fluorescence to fraction of unfolded protein as a function of temperature. For the ERRγ screen, data were collected from 30 to 80° C. at 1° C. intervals and the protein melted under the screening conditions with a characteristic melting temperature, $T_m$, of 52.1° C. Hits were identified from the screen by measuring an increase in the melting temperature of the protein.

In order to estimate binding affinities, it was taken into account that the oligomeric state of ERRγ which is a dimer ($N_2$), and that of a single ligand ($L_f$) can interact per monomer subunit with equal affinity. The melting curve for such a system is described by the following three equilibria:

$$N_2 \xrightarrow{K_u} 2U \quad (1)$$

$$N_2L \xrightarrow{K_{d1}} N_2 + L_f \quad (2)$$

$$N_2L_2 \xrightarrow{K_{d1}} N_2L + L_f \quad (3)$$

The first equilibrium describes the denaturation of ERRγ dimers; the second equilibrium describes the dissociation of the first ligand from the single ligand occupied ERRγ dimers ($N_2L$); and the third equilibrium describes the dissociation of the second ligand from the fully occupied ERRγ dimers ($N_2L_2$).

Following the derivations of Brandts and Lin (*Biochemistry*, 29, 6967, 1990) the dissociation constants for the ligands ($K_{d1}^{T_m}$) can be determined at $T=T_m$ for any ligand concentration $L_t$ by solving numerically the conservation of mass equations:

$$P_t = 2 \times N_2 + 2 \times N_2L + 2 \times N_2L_2 + U \quad (4)$$

$$L_t = N_2L + 2 \times N_2L_2 + L_f \quad (5)$$

and $$L_f = \frac{-b + \sqrt{b^2 - 4 \times a \times c + 2 \times c \times P_t}}{2 \times c} \quad (6)$$

where $$a = \frac{P_t^2}{2 \times K_u} \quad (7)$$

$$b = \frac{P_t^2}{2 \times K_u \times K_{d1}^{T_m}} \quad (8)$$

$$c = \frac{P_t^2}{2 \times K_u \times K_{d1}^{T_m} \times K_{d1}^{T_m}} \quad (9)$$

and $K_u$ is in the unfolding equilibrium constant for ERRγ dimers that is calculated from the melting curve of the protein in the absence of ligand as described by Pantoliano et al. (*J. Biomolecular Screening*, 6, 429, 2001) and Bowie & Sauer (*Biochemistry*, 28, 7139, 1989).

To compare dissociation constants at a common reference temperature, $T_{ref}$, the following equation was used:

$$K_{d1}^{T_m} = \exp\left[\frac{\ln K_d^{ref} - \Delta H_b^{ref} \times (T_m - T_{ref})}{R \times T_{ref} \times T_m}\right] \quad (10)$$

where
$K_d^{ref}$=is the dissociation constant of the ligand at a reference temperature $T_{ref}$
$\Delta H_b^{ref}$=is the binding enthalpy of the ligand to the protein at a reference temperature $T_{ref}$ To solve for $K_{d1}^{T_m}$ from experiments and calculate $K_d^{ref}$, the following input parameters were used:
$\Delta H_u^\circ$=165 kcal/mol and is unfolding enthalpy of the protein at $T=T_m^\circ$ determined by the melting curve of the protein in the absence of ligand
$T_m^\circ$=325.25 K is the melting temperature of the protein in the absence of ligand
$\Delta C_p$=5 kcal/mol-K is the change in heat capacity for the unfolding of the protein in the absence of the ligand
$P_t$=4 µM is the total protein concentration determined by experimental design
$L_t$=100 µM is the total ligand concentration determined by experimental design
$\Delta H_b^{ref}$=−5 kcal/mol is based on reasonable estimates from literature.

In the thermodynamic treatment of the data the following assumptions were made: i) the small ligand interacts only with the folded state of the protein, ii) the reactions are reversible; iii) the unfolding protein reaction is a two-state process and iv) ideal dilute solutions are being used (specific activity for protein and ligands is equal to 1). All fitting and numerical integrations were done using the commercial program MicroMath® Scientist® version 2.01.

A3. TR-FRET Assay

Time-resolved Fluorescence resonance energy transfer (FRET) experiments were performed to examine the functional response of ERRγ ligands. The components of this homogeneous secondary assay included: the ⁶His-tagged-ERRγ LBD (⁶His disclosed as SEQ ID NO: 1), a GST-labeled-hSrc2 co-activator polypeptide and a fluorescent donor/acceptor pair from CIS bio international htrf/bioassays (Bedford, Mass.) using both an α-GST Europium Cryptate (Eu) label and an α⁶His-XL665 (⁶His disclosed as SEQ ID NO: 1) (allophycocyanin) fluorophore.

For FRET measurements, the reaction was buffered in 25 mM Tris pH 8, 2.5 mM Hepes, 20 mM KCl, 1 mM DTT, and 0.05 mg/mL BSA (-lipids). The final concentrations of reagents were 6 nM of ERRγ LBD, 6 nM GST-Src peptide, 30 nM Eu cryptate, and 7.5 nM XL665. Reactions were allowed to reach equilibrium at 25° C. for 4-18 hours before collecting data on the Analyst from LJL Biosystems (Molecular Devices Sunnyvale, Calif.). As a time-resolved method, the samples were excited at 340 nM and emission was collected for 1 ms at both 615 and 665 nm with delays of 400 and 75 μs, respectively. Dose response curves were fitted using a hyperbolic equation and the data reported is the average of three independent experiments.

A4. Isothermal Titration Calorimetry

Binding constants for BPA and ClCH$_3$Ph were measured by using isothermal titration calorimetry. The heat of interaction of the ligands with ERRγ molecules was measured by using the Omega titration calorimeter from Microcal Inc. In a typical titration, 1.4 mL of a 20 μM protein solution is titrated with a ligand solution of ~0.4 mM concentration using a 100 μL syringe by ~20 injections of 5-6 μL each. This syringe is also used to mix the reactants completely in the sample cell by rotating it at 400 rpm. For each injection, the area under the resulting peak is proportional to the heat of interaction, Q. Once this heat is corrected for the titrant dilution and normalized by the titrant solution concentration it becomes equal to the binding enthalpy, $\Delta H_b$, under nonsaturating conditions. The precision of the heat of each injection is about 0.5 μcal. One method of determining $\Delta H_b$ is to average several intermediate peaks from the different sites. In addition to the binding enthalpies, one can obtain binding affinities, and overall stoichiometries of the complexes. The experimental calorimetric binding isotherm is the dependence of the total heat, Qr, (or dQrldX T) on the total concentration of ligand added, Xr. The above three parameters for each type of site are determined iteratively using the Marquardt algorithms as described previously. The initial fitting procedure lets all three parameters float or fixes either the enthalpy, determined independently by averaging the heats of the intermediate peaks of a given site, or n parameters or both until the lowest standard deviation of the fit is obtained; all approaches result in similar values.

A5. Crystallization, Data Collection and Structure Determination

Purified human ERRγ-LBD was buffer exchanged in 20 mM Tris pH 7.5, 0.2M NaCl, 1 mM EDTA, 1 mM DTT and 5% glycerol, complexed with the compound of interest in a 1:2 molar ratio and concentrated to ~11 mg/ml. The protein was screened for crystallization using the hanging-drop vapor diffusion method. The reservoir contained 650 μl of the precipitant solution and the 2 μl hanging drop consisted of a 1:1 protein to precipitant solution ratio. Crystals formed at 277 K from a solution containing 22.6% polyethylene glycol 4000, 0.1M Tris, pH 8.5 and 0.2M Sodium Acetate. Crystals appear and were suitable for data collection the next day (0.2×0.2×0.1 mm). The crystals were transferred to a cryoprotectant solution containing 22.6% polyethylene glycol 4000, 0.1M Tris, pH 8.5, 0.2M Sodium Acetate and 20% glycerol. The crystals were then mounted and quickly frozen by immersion in liquid nitrogen. X-ray diffraction data to a resolution of 2.1 Å for BPA, 2.3 Å for ClCH$_3$Ph and 2.5 Å for 4OHT were collected on a Bruker AXS Proteum 6000 detector. Diffraction data was indexed, integrated and scaled using the Proteum Processing Program suite from Bruker AXS. Under these conditions, the crystals belong to the P4$_1$2$_1$2 space group, with unit cell parameters listed on Table I for each structure. Assuming one ERRγ molecule (28.5 kDa) the crystal volume per protein mass is 2.5, which corresponds to approximately 49.7% solvent content in the crystal. This value is within the range observed for protein crystals [Mathews, 1968].

The structure was determined by molecular replacement using one molecule from the homo dimer structure of ERRγ with the SRC-1 peptide (PDB id 1KV6) as the search model [Greschik, 2002]. Multiple rounds of structure refinement, using the simulated annealing method, followed by the addition of water molecules and resolution extension resulted in the final refinement parameters listed in Table I.

A6. Cell Based Assays

A cell based reporter assay was used to determine the functional response of the ERRγ hits. Transfections were performed in HEK293E cells that were maintained in DMEM supplemented in glutamine and 10% FBS. Co-transfections of 4 μg of a luciferase reporter plasmid and 4 μg of each pBIND-Gal4-ERRγ and pACT-SRC2 plasmids per T-75 flask were done using Lipofectamine as per manufacturers instructions. Twenty-four hours post-transfection, the cells were seeded in 96-well plates at density of 50,000 cells per well in assay media (DMEM phenol free, 5% charcoal stripped FBS). The cells were allowed to adhere to the bottom of the wells approximately 5 hours post-seeding and the compounds were dosed and the final concentration of DMSO was kept below 0.3%. After 24 hours of compound treatment, cells were lysed and treated with the Promega Dual-Glo system. *Firefly Luciferase* activity was read using a luminescence plate reader, and data were normalized against *Renilla luciferase* activity. Data were fitted using subroutines available from GraphPad.

Purified human ERRγ (residues 235-456) was complexed with the compound of interest in a 1:2 ratio. Initial crystals formed at 277 K from a solution containing 22.6% polyethylene glycol 4000, 0.1M Tris, pH 8.5 and 0.2M Sodium Acetate following the hanging drop vapor diffusion method. Crystals appear and were suitable for data collection the next day (0.2×0.2×0.1 mm). X-ray diffraction data to a resolution of 2.1 Å for BPA were collected, indexed, integrated and scaled. Under these conditions, the crystals belong to the P4$_1$2$_1$2 space group, with unit cell parameters a=b=64.07 c=136.48 Å. The structure was determined by molecular replacement using one molecule from the homo dimmer structure of ERRγ with the SRC-1 peptide (PDB id 1KV6) as the search model [Greschik, 2002].

B. Results and Discussion

B1. Identification of Ligands that Stabilize ERRγ and Determination of Binding Affinities.

ThermoFluor® is a miniaturized thermal shift assay that studies and exploits the well-described phenomenon of ligand induced stabilization of macromolecules. Ligand binding energy adds directly to the ground state energy of a macromolecule and results in increased thermal stability. The degree of stabilization is proportional to the binding affinity of the ligand for the macromolecule. We expressed and characterized biochemically and biophysically the ligand binding domain of ERRγ as part of our protein characterization prior to screening by using the ThermoFluor® platform. The protein under our experimental conditions (concentration 4 μM and higher) behaves as a dimer as judged by size exclusion chromatography and dynamic light scattering with apparent molecular weights of 61 and 52 kDa respectively. Further biophysical characterization using thermal denaturation methods by monitoring loss of α-helicity by CD spectroscopy, shows that the protein melts in a cooperative fashion over a narrow temperature range, and a positive thermal stabilization is observed in the presence of the reported antagonist 4OHT (data not shown). The protein solution conditions were further optimized for a ThermoFluor® screen. We measured the effect of ligands on the thermal stability of ERRγ by measuring the fraction of unfolded protein as a function of temperature using the environmentally sensitive dye ANS as a reporter that is incorporated in the screening buffer. Approximately 3,000 compounds were screened against this receptor. The collection of compounds screened contained a generic drug collection, bioactive molecules (fatty acids and steroids) and known estrogenic compounds. FIG. 1 shows that several compounds were found to produce a positive stabilization of the receptor up to 5° C. and a subset of them are disclosed in Table II.

Table III shows the calculated affinities of the respective ligands from Table II against this nuclear receptor panel and the method for calculating the affinities is described in the material and methods section and additional details on the thermodynamic parameters are provided in the footnote of Table III. These calculations take into account that the melting of the NHR's is a two-state process and that we are measuring the denaturation of a dimer to an unfolded protein and that the reaction is reversible. The determined binding constants calculated in such way are estimates and reflect the induced ligand stabilization of the receptors. These values are provided so that meaningful comparisons can be made among observed $\Delta Tm$ changes and binding constants at some reference state, since the reported affinities are dependent on the observed induced stabilization and the ground state of the ligand free receptor (equation 10).

Several classes of compounds were found to stabilize ERRγ. The majority of the compounds interacted weakly with micro-molar affinities (Table II), but for some, sub-micromolar estimates were obtained; including BPA, an endocrine disruptor (Quesada, Fuentes et al. 2002), ClCH$_3$Ph, a potent activator of Ca$^{2+}$ release from the sarcoplasmic reticulum of skeletal muscle (Zorzato, Scutari et al. 1993), and the previously reported estrogen receptor antagonist 4OHT (Coward, Lee et al. 2001). Counter-screening against the other two members of the ERR subfamily (ERRα & ERRβ) did not result in any appreciable stabilization of the receptors with the exception of 4OHT against ERRS, and as expected all natural and synthetic estrogenic ligands stabilized ERα and ERβ. In addition, we found that the isoflavones daizdein and genistein did not interact with any of the ERR's, in contrast to a previous study where they were reported as agonist for ERRα (Suetsugi, Su et al. 2003). Estradiol and derivatives stabilized ERRγ marginally with 17-α-estradiol being the most potent characterized by single digit micromolar bind affinity. Moras & Renaud have demonstrated the weak association of estradiol to ERRγ using non-denaturing mass-spectroscopic methods (Greschik, Wurtz et al. 2002) and recently published the presence of a fortuitous co-crystallized cholate molecule in the ERRγ-4OHT complex (Greschik, Flaig et al. 2004). The implication of the interaction of these steroid ligands is not known since the concentration required to interact with the receptor are supra-physiological.

B2. Hit Profiling of BPA and ClCH$_3$Ph

Figure 2A:
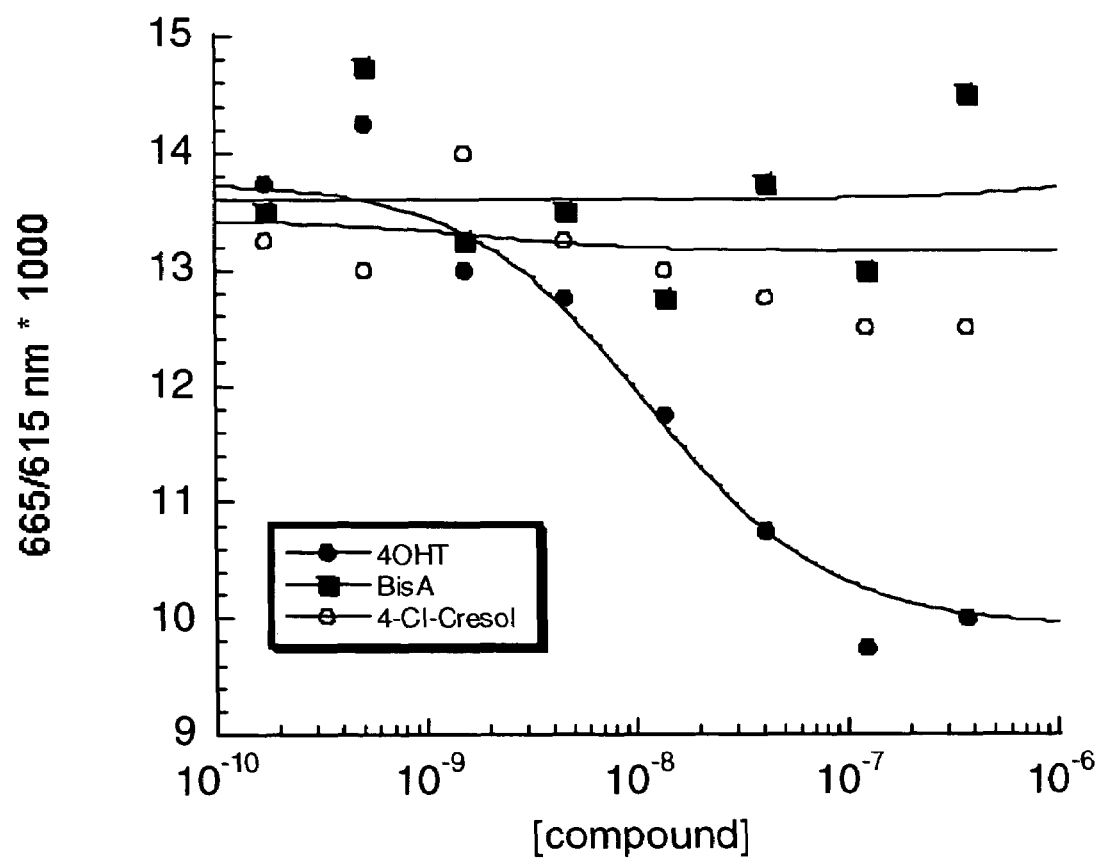
FIG. 2.
Figure 2B:
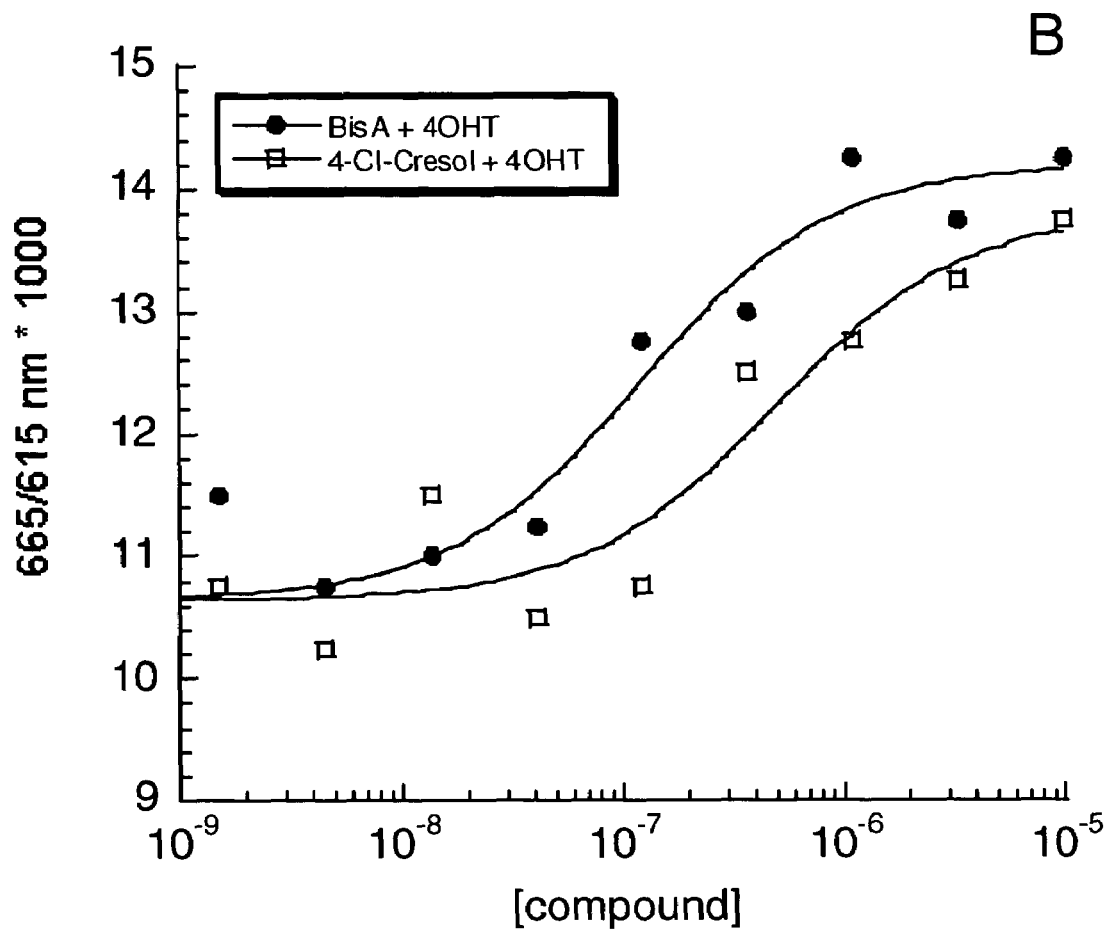

We employed a TR-FRET based assay to functionally characterize BPA and ClCH$_3$Ph. ERRγ is regarded as a constitutive active receptor and has the ability to recruit co-activator peptides in the absence of an agonist ligand. FIG. 2A shows that neither ligand displaced co-activator peptide bound to the receptor, in contrast with 4OHT that displaced the peptide fragment with an affinity of ~11 nM. FIG. 2B shows that in the presence of 4OHT, both ligands were competitive for 4OHT as monitored by the association of the peptide to receptor with EC$_{50}$ values of 120 and 500 nM, respectively. Binding of these ligands was also observed by isothermal titration calorimetry, which was characterized by highly exothermic binding enthalpies ($\Delta H_b$ ~−21 kcal/mol) and affinities of 70 and 380 nM, respectively. We were not able to demonstrate an enhancement in the affinity of the receptor for co-activator peptide fragments or a change in transcriptional activity in a trans-activation cellular assay. Therefore, both ligands are potent for ERRγ and competitive for binding at the 4OHT binding site but functionally silent.

B3. Overall Structure

ERRγ was co-crystallized with BPA and ClCH$_3$Ph in an attempt to understand the molecular basis of the functional silent nature of these two ligands. All of our ERRγ structures crystallized in the P4$_1$2$_1$2 space group with one molecule in the asymmetric unit. A crystallographic two fold generates the functional homo dimer observed in all previously published ERRγ structures. The LBP is formed mostly by hydrophobic residues and surrounded by an α-helical bundle and one small beta sheet. The few polar residues comprising the LBD include R316, E275, and N346, which make hydrogen bond interactions with the ligands.

Analysis of the determined ERRγ structures shows conserved arrangement of secondary structural elements, compared to previously determined ERR and ER structures. In particular the H8/H9 loop is eight residues shorter in ERRγ, compared to ERα shifting H9 by half a turn. One major difference between ERs and ERRs lies in the residue at position 476, a Phe in ERRs and a Leu in ERs. This makes the cavity of ERRs smaller, limiting the size of compounds that can bind. An overlay between the ERα-estradiol structure and Erβ-genistein shows that both ligands would not be able to fit in the cavity without causing major secondary structure rearrangement.

B4. Agonist Structures

Figure 3:
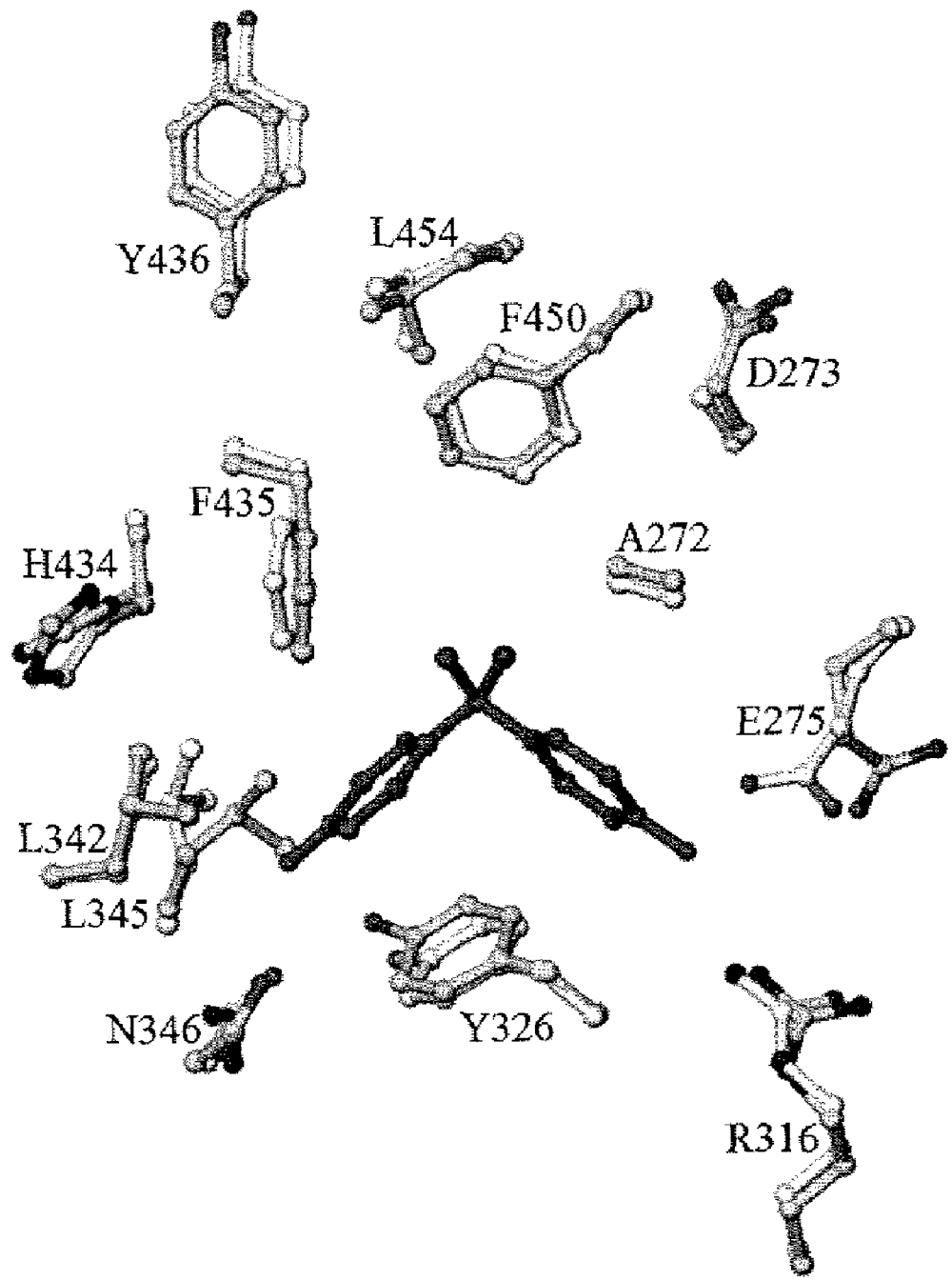
FIG. 3.
Figure 4:
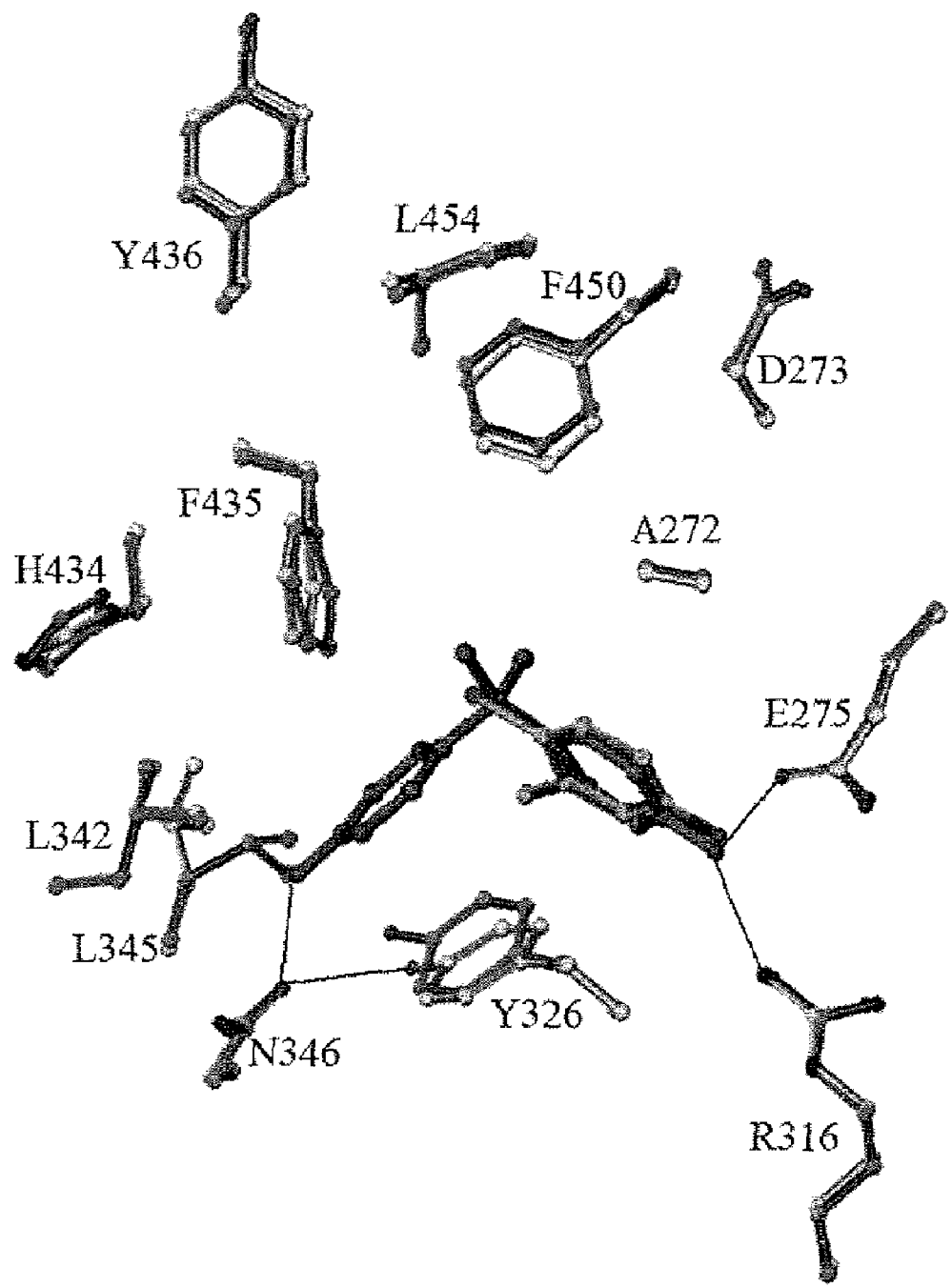
FIG. 4.
Figure 5:
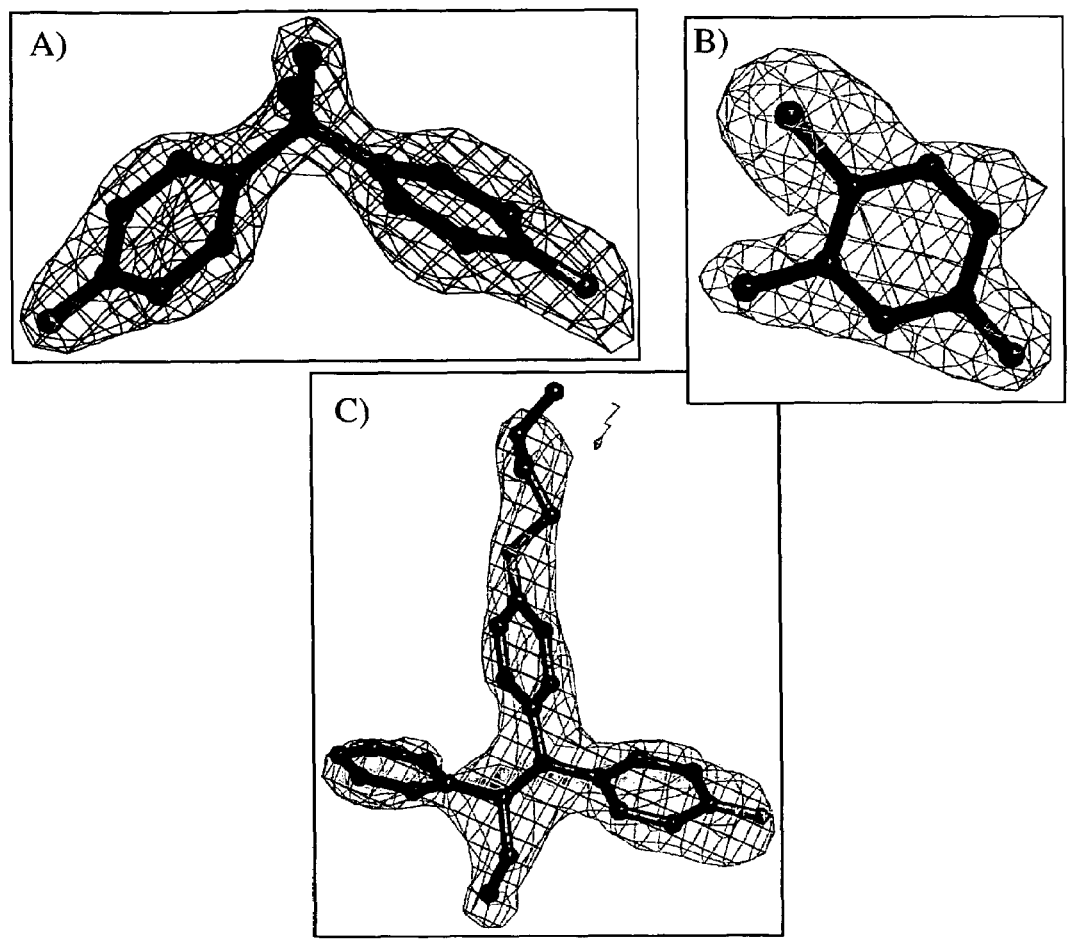
FIG. 5.
Figure 6A:
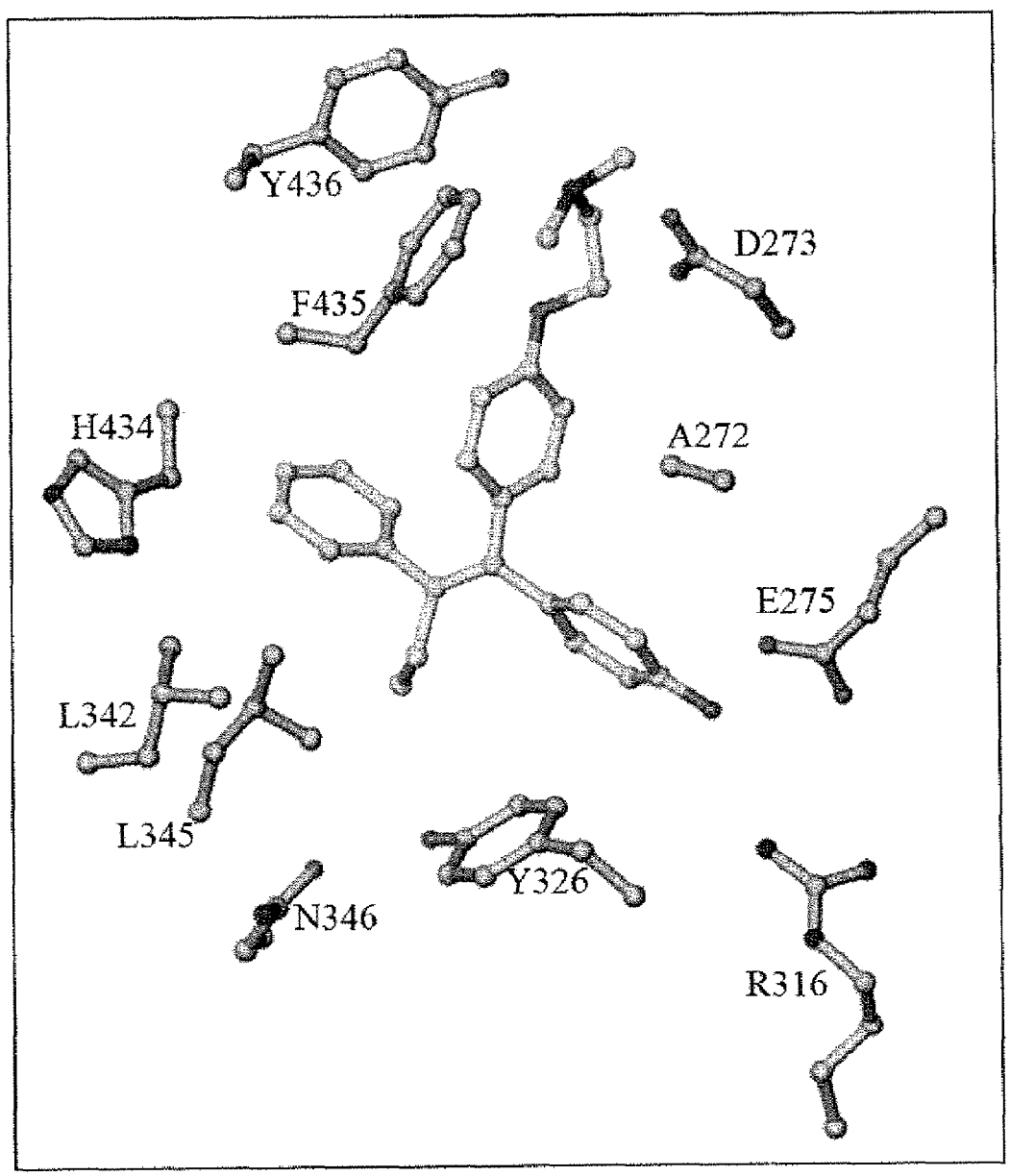
FIG. 6A shows some of the ERRγ residues that delineate the LBP. Hydrogen bonds between the phenyl group and L275 and R316 and between the amine and D273 hold the ligand in position. ERRγ-4OHT residues shown in medium gray and 4OHT ligand in light gray with atoms colored by element nitrogen (black) and oxygen (dark gray).
Figure 6B:
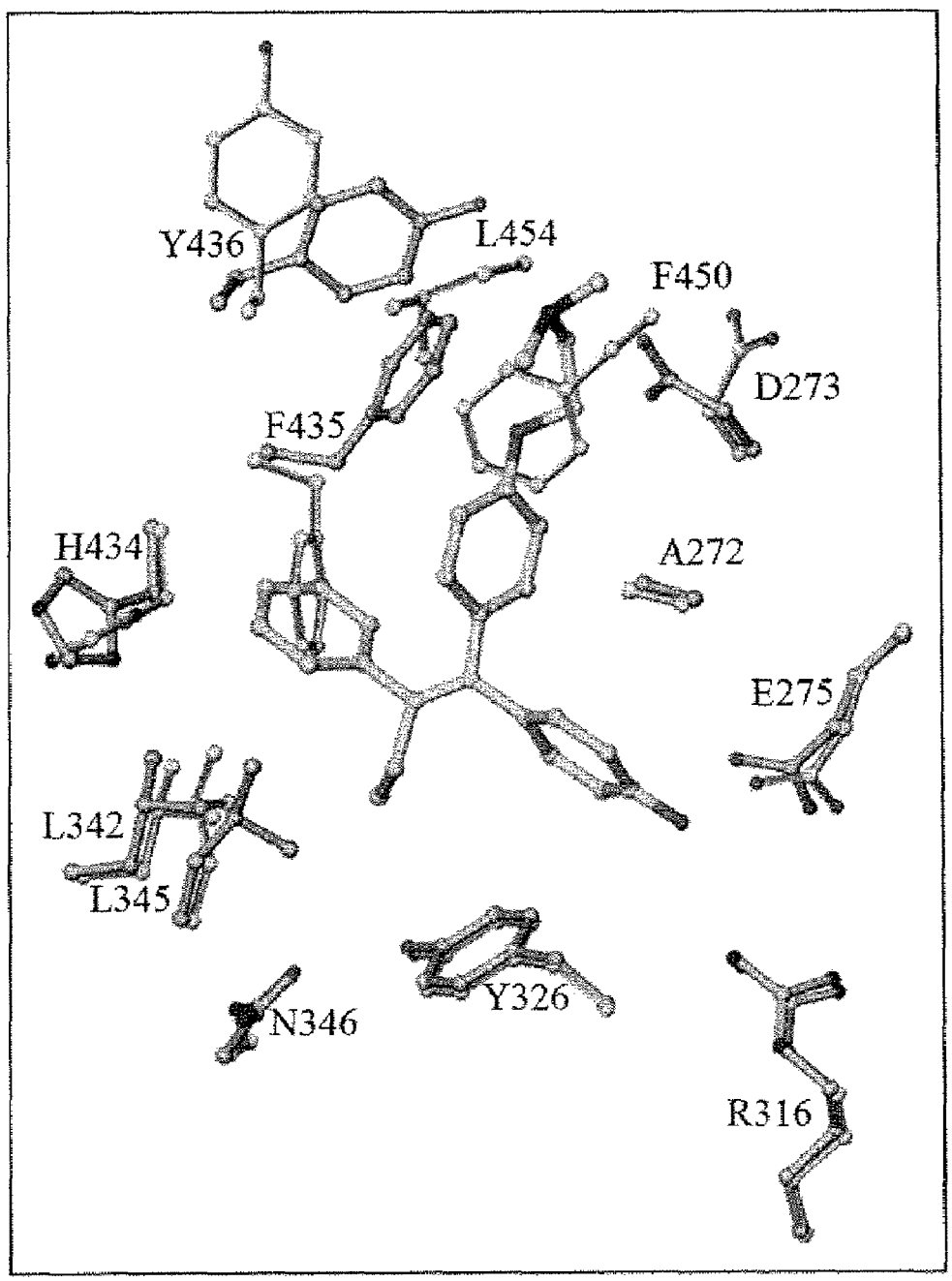
FIG. 6B shows overlay of the LBPs of ERRγ-BPA over ERRγ-4OHT. Residues F450 and L454 not observed in the ERRγ- 4OHT structure are part of H12. Diagram shows collision of ligand with F435 and F450 and of residue F435 with L454. Side chain of residue D273 reorients to make contact with 4OHT's amine. ERRγ-4OHT residues shown in medium gray, ERRγ-BPA residues in light medium gray and 4OHT ligand in light gray with atoms colored by element nitrogen (black) and oxygen (dark gray).

ERRγ adopts an active conformation without a bound ligand, a characteristic only observed in orphan nuclear receptors (Greschik, Wurtz et al. 2002). Table IV shows the atomic coordinates for the ERRγ-Bisphenol A co-crystal structure. FIG. 3 shows, that at a close look into the active site of the ERRγ-BPA structure shows that the hydroxyl groups of the ligand are within hydrogen bonding distance of residues N346, R316 and E275. A hydrogen bond between Y326 and N346 holds N346 in position to interact with the second phenyl ring of BPA. The asparagine at position 346 in ERRγ is not conserved among nuclear receptors (ERRα (Gly), ERRβ (Tyr), ERα (Phe) and ERβ (Phe)). This asparagine makes the N346-OH interaction specific to ERRγ, compared to the other ERs and ERRs. This interaction is currently being exploited in our SBDD efforts to achieve specificity over the other ERs and ERRs. The highly hydrophobic pocket of ERRγ provides a favorable environment for the phenyl rings and methyl groups in BPA and ClCH$_3$Ph. Table V shows the atomic coordinates for the ERRγ-ClCH$_3$Ph co-crystal structure. FIG. 4 shows the structure of ERRγ with ClCH$_3$Ph and reveals interactions between the phenyl oxygen of the ligand and residues E275 and R316. This interaction is also observed in the BPA structure. FIG. 5 illustrates the final 2Fo-Fc electron density map of the three ligands discussed herein.

FIG. 3 shows that the structures of the two functionally silent ligands, BPA and ClCH$_3$Ph, present a conserved position for the active site residues between the apo and ligand bound structures. An overlay of the ERRγ-steroid receptor coactivator-1 (SRC) peptide (pdb id 1KV6) onto ERRγ-BPA showed no conformational change throughout the main chain. Side chain movement is observed in a few residues. Residue E275 reorients to maximize hydrogen bond interactions with the ligand. FIG. 3 shows that the side chain of L345 moves away from the pocket upon BPA binding, opening up the cavity and making room for the second phenyl ring of BPA [Greschik, 2002]. A comparison of the residues involved in the coactivator binding in the ERRγ agonist structures and the ERRγ-SRC peptide structure reveals that the orientation of those residues is conserved. Moreover, modeling of the SRC peptide into our ERRγ-BPA structures reveals that these ligand bound structures will allow for coactivator peptide binding. This is consistent with the fact that these ligands do not enhance or disrupt co-activator binding.

A comparison between our structures and the recently published ERRα structure shows a very similar C alpha trace and a ligand binding pocket much smaller for ERRα compared to ERRγ. The cavity size in ERRα is reduced by the substitution of two alanines (A272 and A431) in ERRγ by a phenylalanine (F328) and a valine (V491), respectively. An overlay of our ERRγ agonist structures revealed that neither BPA nor ClCH$_3$Ph will be able to fit in ERRα's cavity.

B5. Antagonist Binding

Figure 7:
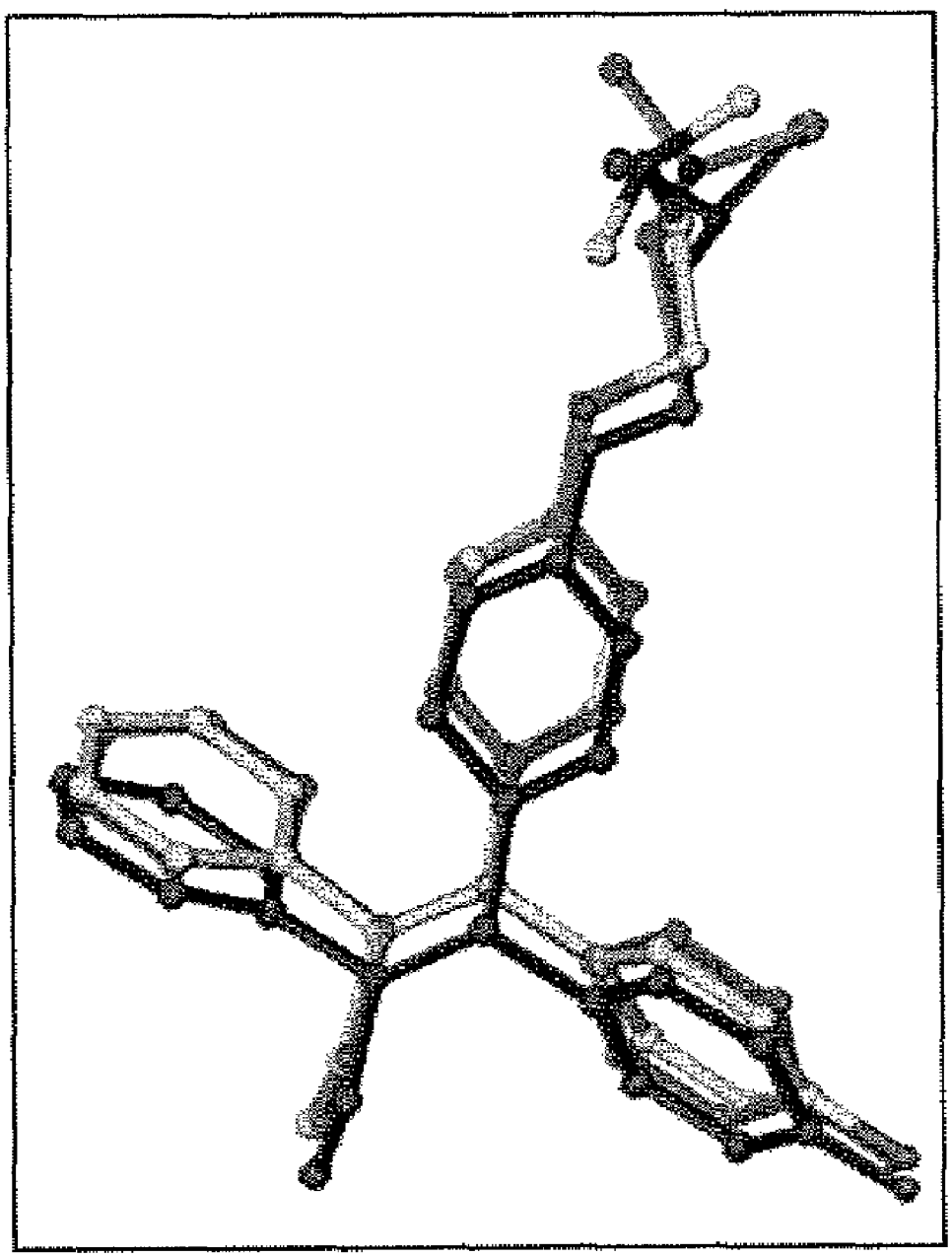
FIG. 7.

Table IV shows the atomic coordinates for the ERRγ-Bisphenol A co-crystal structure. FIG. 7 shows the X-ray structure of ERRγ with 4OHT and reveals the displacement of H12 from the position essential for coactivator binding resulting in an inactive protein conformation. Interactions between 4OHT and ERRγ are shown in FIG. 7. Hydrogen bonds with E275 and R316, also observed in the agonist structures hold the ligand in position.

The antagonist mechanism of 4OHT can be explained by comparing ligand binding and side chain rearrangement between this structure and the previously presented agonist structures. The benzyl group of 4OHT pushes F435 out of the cavity towards Y436, making hydrophobic interactions (π-π stacking) between both rings and opening up the cavity to make room for the larger ligand (FIG. 7). Once F435 reorients, it collides with L454 in H12, forcing H12 to move out of its coactivator binding position. Moreover, the end part of the long 4OHT molecule collides with F450, also part of H12. Initially, it was thought that the long and bulky 4OHT molecule was solely responsible for the displacement of H12, but a recently determined structure of the smaller antagonist diesthylstilbestrol, displays the same antagonistic behavior (Greschik, Flaig et al. 2004). This smaller molecule does not collide with F450. The reorientation of F435 suggests to be the event responsible for ERR's inhibition.

A comparison between the ERRγ-4OHT and the agonist structures presented in this study shows residues 441 to 456, observed in the BPA and ClCH$_3$Ph structures, are no longer observed in the 4OHT structure as it is part of the now disordered H12. Also, the side chain of L345 adapts to fit a different size of ligand. The ERRγ-4OHT structure shows L345 moving toward the empty space previously occupied by the second phenol ring of BPA. The shifting of the side chain of L345 is also observed in the Apo ERRγ-SRC structure and in with our ClCH$_3$Ph.

Figure 8:
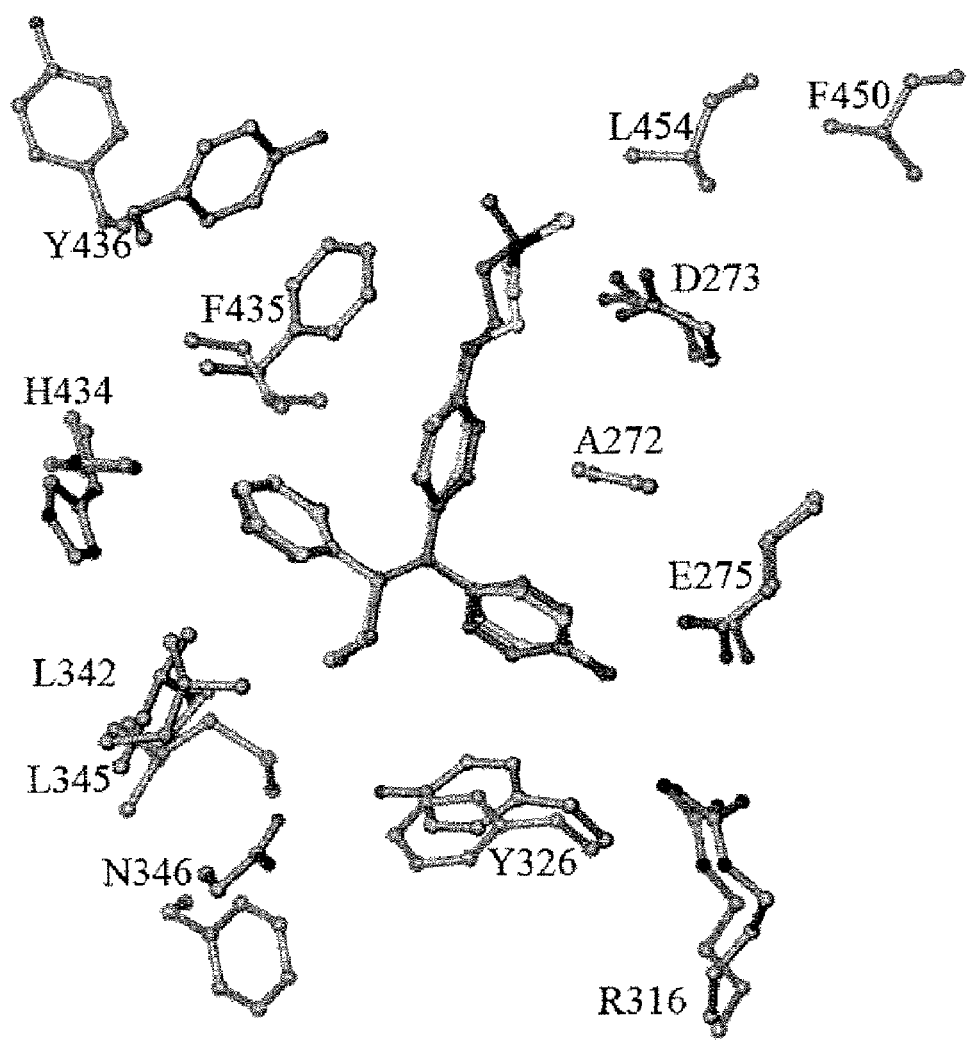
FIG. 8.

The previously published ERRγ-4OHT structure by Greschik's et al presented an ERRγ-4OHT structure with H12 packed against the LBP of a neighboring molecule unlike our structure, which has a disordered H12 (Greschik, Flaig et al. 2004). His analysis of the structure indicated that this orientation is due to crystal packing and has no physiological significance. Our structure in a different space group confirms his analysis. On the other hand, the ERα-4OHT structure has H12 remaining in its coactivator binding position upon 4OHT binding (Shiau, Barstad et al. 1998). FIG. 8 shows the wider cavity of ERα with a leucine (L525) in ERRγ's F435 position which leaves enough space in the cavity for 4OHT binding and shows no collisions with H12.

An overlay of the 4OHT molecules from Greischick's ERRγ-4OHT structure, ERα-4OHT and our ERRγ structure shows a conserved orientation between the three with the most apparent difference in the orientation of the amino group of the 4OHT molecule (FIG. 8). The structure of ERα with 4OHT reveals H12 packing against H3 and H4 occupying the place of the activation peptide according to the ERRγ-SRC and ERRα-PGC-1-a peptide structures. These structures and its secondary structure rearrangement demonstrate that antagonism relies on the rearrangement of the H12 and not on ligand binding. The flexibility observed in H12 and its ability to move allows it to regulate proteins activity.

B6. Conclusion

Current approaches to validate the therapeutic utility of a target for the treatment of a disease rely on genomic data and annotating function by sequence analysis. Once a target is validated then chemical libraries can be selected or synthesized that are centered on known chemotypes for the particular function of the target and assayed with conventional methods. Conventional assay development is problematic for orphan targets since they rely on competitive displacement of a known ligand or rely on a functional response. With ThermoFluor®, assay development for an orphan protein is not problematic (Grasberger, Lu et al. 2005). Ligands that will interact with the protein will be identified because they will produce a positive stabilization of the protein. If the stabilizing ligand is a biochemical, then a putative function can be assigned to the orphan protein and a biochemical, functional or cell-based assay can be designed to elucidate the biology of the protein. The utility of ThermoFluor® in identifying ligands that stabilize ERRγ, an orphan nuclear receptor, has been demonstrated. Crystallography has been used to define the molecular basis of the functionally silent response of BPA and ClCH$_3$Ph in our cellular trans-activation and co-activator TR-FRET assays. The diversity of ligands that were found to interact with this receptor raises the possibility of the existence of a natural ligand that can regulate the activity of ERRγ. These putative ligands will not act as classical agonist for nuclear receptors do, since ERRγ is regarded to be constitutively active. Stabilization of the receptor can alter the steady state levels or phosphorylation levels of the receptor can occurr. Either of these events can impact biological activity through cross-talk to other nuclear receptors (Kojo, Tajima et al. 2006), alter affinity for response elements (Barry and Giguere 2005) or specific co-regulator interactions (Barry, Laganiere et al. 2006).

These ERRγ/Bisphenol A and ERRg/chlorocresol structures provide tools for the design of selective agonist and antagonist molecules for ERRγ. Specifically the hydrogen bond between Y326 and N346 holds N346 in position to interact with BPA's second phenyl ring. ERRγ's asparagine at position 346 is not conserved among nuclear receptors (ERRα (Gly), ERRβ (Tyr), ERα (Phe) and ERβ (Phe)). This asparagine makes the N346-OH interaction specific to ERRγ, compared to the other ERs and ERRs. This interaction can be employed to achieve specificity over the other ERs and ERRs and develop chemical tools that can enhance our understanding of the biology of ERRg by altering genes expression levels that are regulated by this receptor with the use of selective agonist and antagonist small molecules.

TABLE I

Refinement Parameters

| Parameter | BPA | ClCH3Ph | 4OHT |
|---|---|---|---|
| Unit cell, Å | a = b = 64.07 | a = b = 64.28 | a = b = 64.00 |
|  | c = 136.48 | c = 137.18 | c = 137.95 |
| Resolution, Å | 2.1 | 2.3 | 2.5 |
| Completeness, % |  |  |  |
| Rmerge[¥], % | 4.8 (14.0) | 11.8 (29.2) | 9.0 (30.1) |
| $<I>/<\sigma_I>$ | 11.7 (4.3) | 5.9 (1.5) | 5.8 (1.5) |
| Rfactor[#], % | 21.0 | 20.51 | 21.3 |
| Rfree[¶], % | 26.0 | 25.64 | 26.3 |
| Bfactor$_{avg}$ | 18.0 | 10.50 | 21.3 |
| Rmsd^ bonds, Å |  |  |  |
| Rmsd angles, ° |  |  |  |

Values in parenthesis refer to the highest resolution shell

[¥] $R_{merge} = \Sigma_{hkl} \Sigma_I (|I_I - <I>|)$, where $I_I$ is an individual intensity measurement and $<I>$ is the average intensity for this reflection, with summation over all data.

[#] Rfactor = $\Sigma ||F_o| - |F_c||/\Sigma |F_o|$.

[¶] 10% of the total reflections withheld.

^ Root mean square deviation

TABLE II

Thermal Stabilization of ERR's and ER's against the Functional Probe Library.[a]

| Ligand class | ERRα | ERRβ | ERRγ | ERα | ERβ |
|---|---|---|---|---|---|
| Phenol/Polyphenol | | | | | |
| BPA | 0.0 | −0.1 | 5.5 | 4.4 | 7.4 |
| ClCH3Ph | 0.1 | 0.2 | 3.9 | 0.4 | 2.4 |
| 4-bromocresol | 0.1 | 0.5 | 4.3 | ND | ND |
| 4chloro-3ethyl-phenol | 0.2 | 0.4 | 4.1 | ND | ND |
| Steroid | | | | | |
| 17-β-estradiol | 0.1 | −0.1 | 0.6 | 14.8 | 17.5 |
| 17-α-estradiol | −0.1 | 0.0 | 1.3 | 10.4 | 12.8 |
| 2-methoxy-estradiol | 0.1 | −0.1 | 0.0 | 3.5 | 2.9 |
| estrone | 0.0 | −0.2 | 0.8 | 7.7 | 11.3 |
| 17-α-ethynyl-estradiol | 0.3 | −0.4 | 1.6 | 15.5 | 15.3 |
| 4-estrene-3-α-17-β-diol | 0.0 | −0.1 | −0.1 | 4.9 | 7.7 |
| Small synthetic ligands | | | | | |
| DES | −0.1 | 0.5 | 2.7 | 12.0 | 18.9 |
| tamoxifene | −0.1 | −0.1 | 2.7 | 8.5 | 9.8 |
| 4OHT | −0.1 | 2.15 | 5.7 | 17.1 | 18.2 |
| clomiphene | −0.1 | −0.1 | 0.7 | 8.4 | 9.7 |
| raloxifene | 0.1 | 0.0 | 0.0 | 16.7 | 11.9 |
| DPN | −0.2 | 0.2 | 0.3 | 5.5 | 11.7 |
| PPT | −2.3 | −3.5 | −1.8 | 11.7 | 9.5 |
| Genistein | 0.0 | 0.1 | 0.1 | 7.4 | 13.9 |
| Daidzein | 0.0 | 0.3 | −0.1 | 4.1 | 8.9 |
| ICI-182780 | 0.0 | 0.0 | 0.0 | 13.9 | 16.7 |
| resvesterol | 0.0 | 0.2 | 0.4 | ND | ND |

[a] ThermoFluor® melts were performed in 25 mM HEPES pH 8.0, 100 mM NaCl, 1 mM EDTA, 0.1 mg/mL protein, 25 μM ANS, 2% DMSO and the final concentration of test compound was 100 μM. Melting temperatures, $T_m$, under these experimental conditions for ERRα, ERRβ, ERRγ, ERα and ERβ, were, 54.4, 47.5, 49.6, 39.1 and 41.1 °C. respectively. $\Delta T_m$ values are the change of melting temperature for the free protein in the presence of excess test compound.

TABLE III

Estimated Dissociation constants for ligands against ERR's and ER's receptors[a]

| Ligand class | ERRα | ERRβ | ERRγ | ERα | ERγ |
|---|---|---|---|---|---|
| Phenol/Polyphenol | | | | | |
| BPA | — | — | 2.97E−07 | 1.64E−06 | 1.79E−07 |
| ClCH3Ph | — | — | 7.88E−07 | 3.73E−05 | 3.05E−06 |
| 4-bromocresol | — | 1.72E−05 | 6.33E−07 | ND | ND |
| 4chloro-3ethyl-phenol | — | 1.80E−05 | 7.22E−07 | ND | ND |
| Steroid | | | | | |
| 17-β-estradiol | — | — | 1.99E−05 | 6.87E−09 | 4.63E−10 |
| 17-α-estradiol | — | — | 6.36E−06 | 7.62E−08 | 8.39E−09 |
| 2-methoxy-estradiol | — | — | — | 2.66E−06 | 2.31E−06 |
| estrone | — | — | 1.33E−05 | 3.04E−07 | 2.05E−08 |
| 17-α-ethynyl-estradiol | — | — | 4.29E−06 | 4.47E−09 | 1.86E−09 |
| 4-estrene-3-α-17-β-diol | — | — | — | 1.27E−06 | 1.57E−07 |
| Small synthetic ligands | | | | | |
| DES | — | 1.49E−05 | 1.73E−06 | 3.15E−08 | 1.91E−10 |
| tamoxifene | — | — | 1.72E−06 | 2.02E−07 | 4.89E−08 |
| 4OHT | — | 2.64E−06 | 2.62E−07 | 1.83E−09 | 3.00E−10 |
| clomiphene | — | — | 1.56E−05 | 2.10E−07 | 5.21E−08 |
| raloxifene | — | — | — | 2.27E−08 | 1.46E−08 |
| DPN | — | — | — | 9.00E−07 | 1.65E−08 |
| PPT | — | — | — | 3.87E−08 | 5.83E−08 |
| Genistein | — | — | — | 3.48E−07 | 4.45E−09 |
| Daidzein | — | — | — | 1.87E−06 | 8.15E−08 |
| ICI-182780 | — | — | — | 1.13E−08 | 7.89E−10 |
| resvesterol | — | — | — | ND | ND |

[a] Calculated dissociation constants at reference temperature 25° C. determined from the induced thermal stabilization values reported in Table II. Details on how $K_d$ values are obtained appear in Material and Method section. $\Delta H_u$ enthalpies for the unfolding of ERRα, ERRβ, ERRγ, ERα and ERγ were 190, 155, 165, 112 and 122 kcal/mol respectively.

Lengthy table referenced here

US07655756-20100202-T00001

Please refer to the end of the specification for access instructions.

Lengthy table referenced here

US07655756-20100202-T00002

Please refer to the end of the specification for access instructions.

Lengthy table referenced here

US07655756-20100202-T00003

Please refer to the end of the specification for access instructions.

REFERENCES

Aranda, A. and A. Pascual (2001). "Nuclear hormone receptors and gene expression." *Physiol Rev* 81(3): 1269-304.

Ariazi, E. A., G. M. Clark, et al. (2002). "Estrogen-related receptor alpha and estrogen-related receptor gamma associate with unfavorable and favorable biomarkers, respectively, in human breast cancer." *Cancer Res* 62(22): 6510-8.

Barry, J. B. and V. Giguere (2005). "Epidermal growth factor-induced signaling in breast cancer cells results in selective target gene activation by orphan nuclear receptor estrogen-related receptor alpha." *Cancer Res* 65(14): 6120-9.

Barry, J. B., J. Laganiere, et al. (2006). "A single nucleotide in an estrogen-related receptor alpha site can dictate mode of binding and peroxisome proliferator-activated receptor gamma coactivator 1alpha activation of target promoters." *Mol Endocrinol* 20(2): 302-10.

Blumberg, B. and R. M. Evans (1998). "Orphan nuclear receptors—new ligands and new possibilities." *Genes Dev* 12(20): 3149-55.

Busch, B. B., W. C. Stevens, Jr., et al. (2004). "Identification of a selective inverse agonist for the orphan nuclear receptor estrogen-related receptor alpha." *J Med Chem* 47(23): 5593-6.

Carrier, J. C., G. Deblois, et al. (2004). "Estrogen-related receptor alpha (ERRalpha) is a transcriptional regulator of apolipoprotein A-IV and controls lipid handling in the intestine." *J Biol Chem* 279(50): 52052-8.

Chawla, A., J. J. Repa, et al. (2001). "Nuclear receptors and lipid physiology: opening the X-files." *Science* 294(5548): 1866-70.

Coward, P., D. Lee, et al. (2001). "4-Hydroxytamoxifen binds to and deactivates the estrogen-related receptor gamma." *Proc Natl Acad Sci USA* 98(15): 8880-4.

Escriva, H., F. Delaunay, et al. (2000). "Ligand binding and nuclear receptor evolution." *Bioessays* 22(8): 717-27.

Giguere, V. (1999). "Orphan nuclear receptors: from gene to function." *Endocr Rev* 20(5): 689-725.

Giguere, V. (2002). "To ERR in the estrogen pathway." *Trends Endocrinol Metab* 13(5): 220-5.

Giguere, V., N. Yang, et al. (1988). "Identification of a new class of steroid hormone receptors." *Nature* 331(6151): 91-4.

Glass, C. K. (2006). "Going nuclear in metabolic and cardiovascular disease." *J Clin Invest* 116(3): 556-60.

Grasberger, B. L., T. Lu, et al. (2005). "Discovery and cocrystal structure of benzodiazepinedione HDM2 antagonists that activate p53 in cells." *J Med Chem* 48(4): 909-12.

Greschik, H., R. Flaig, et al. (2004). "Structural basis for the deactivation of the estrogen-related receptor gamma by diethylstilbestrol or 4-hydroxytamoxifen and determinants of selectivity." *J Biol Chem* 279(32): 33639-46.

Greschik, H., J. M. Wurtz, et al. (2002). "Structural and functional evidence for ligand-independent transcriptional activation by the estrogen-related receptor 3." *Mol Cell* 9(2): 303-13.

Greschik, H., Wurtz, J., et al. (2002). "ERRγ complexed with a steroid receptor coactivator-1 (SRC-1) peptide." *Mol Cell* 9: 303.

Greschik, H., Flaig, R., et al. (2004). "ERRγ in complex with diethylstillbestrol and the ERRγ-40HT complex structure." *J Biol Chem* 279: 336-39.

Heard, D. J., P. L. Norby, et al. (2000). "Human ERRgamma, a third member of the estrogen receptor-related receptor (ERR) subfamily of orphan nuclear receptors: tissue-specific isoforms are expressed during development and in the adult." *Mol Endocrinol* 14(3): 382-92.

Heyman, R. A., D. J. Mangelsdorf, et al. (1992). "9-cis retinoic acid is a high affinity ligand for the retinoid X receptor." *Cell* 68(2): 397-406.

Hong, H., L. Yang, et al. (1999). "Hormone-independent transcriptional activation and coactivator binding by novel orphan nuclear receptor ERR3." *J Biol Chem* 274(32): 22618-26.

Horard, B. and J. M. Vanacker (2003). "Estrogen receptor-related receptors: orphan receptors desperately seeking a ligand." *J Mol Endocrinol* 31(3): 349-57.

Huss, J. M., I. P. Torra, et al. (2004). "Estrogen-related receptor alpha directs peroxisome proliferator-activated receptor alpha signaling in the transcriptional control of energy metabolism in cardiac and skeletal muscle." *Mol Cell Biol* 24(20): 9079-91.

Johnston, S. D., X. Liu, et al. (1997). "Estrogen-related receptor alpha 1 functionally binds as a monomer to extended half-site sequences including ones contained within estrogen-response elements." *Mol Endocrinol* 11(3): 342-52.

Kamei, Y., H. Ohizumi, et al. (2003). "PPARgamma coactivator 1beta/ERR ligand 1 is an ERR protein ligand, whose expression induces a high-energy expenditure and antagonizes obesity." *Proc Natl Acad Sci USA* 100(21): 12378-83.

Kliewer, S. A., J. M. Lehmann, et al. (1999). "Orphan nuclear receptors: shifting endocrinology into reverse." *Science* 284(5415): 757-60.

Kojo, H., K. Tajima, et al. (2006). "A novel estrogen receptor-related protein gamma splice variant lacking a DNA binding domain exon modulates transcriptional activity of a moderate range of nuclear receptors." *J Steroid Biochem Mol Biol*.

Kraus, R. J., E. A. Ariazi, et al. (2002). "Estrogen-related receptor alpha 1 actively antagonizes estrogen receptor-regulated transcription in MCF-7 mammary cells." *J Biol Chem* 277(27): 24826-34.

Kumar, R., B. H. Johnson, et al. (2004). "Overview of the structural basis for transcription regulation by nuclear hormone receptors." *Essays Biochem* 40: 27-39.

Luo, J., R. Sladek, et al. (2003). "Reduced fat mass in mice lacking orphan nuclear receptor estrogen-related receptor alpha." *Mol Cell Biol* 23(22): 7947-56.

Matulis, D., J. K. Kranz, et al. (2005). "Thermodynamic stability of carbonic anhydrase: measurements of binding affinity and stoichiometry using ThermoFluor." *Biochemistry* 44(13): 5258-66.

Mootha, V. K., C. Handschin, et al. (2004). "Erralpha and Gabpa/b specify PGC-1alpha-dependent oxidative phosphorylation gene expression that is altered in diabetic muscle." *Proc Natl Acad Sci USA* 101(17): 6570-5.

Moras, D. and H. Gronemeyer (1998). "The nuclear receptor ligand-binding domain: structure and function." *Curr Opin Cell Biol* 10(3): 384-91.

Olefsky, J. M. (2001). "Nuclear receptor minireview series." *J Biol Chem* 276(40): 36863-4.

Pantoliano, M. W., E. C. Petrella, et al. (2001). "High-density miniaturized thermal shift assays as a general strategy for drug discovery." *J Biomol Screen* 6(6): 429-40.

Quesada, I., E. Fuentes, et al. (2002). "Low doses of the endocrine disruptor bisphenol-A and the native hormone 17beta-estradiol rapidly activate transcription factor CREB." *Faseb J* 16(12): 1671-3.

Rentzeperis, D., L. A. Marky, et al. (1995). "Interaction of minor groove ligands to an AAATT/AATTT site: correlation of thermodynamic characterization and solution structure." *Biochemistry* 34(9): 2937-45.

Rosen, J., K. Marschke, et al. (2003). "Nuclear hormone receptor assays for drug discovery." *Curr Opin Drug Discov Devel* 6(2): 224-30.

Schreiber, S. N., R. Emter, et al. (2004). "The estrogen-related receptor alpha (ERRalpha) functions in PPARgamma coactivator 1alpha (PGC-1alpha)-induced mitochondrial biogenesis." *Proc Natl Acad Sci USA* 101(17): 6472-7.

Shiau, A. K., D. Barstad, et al. (1998). "The structural basis of estrogen receptor/coactivator recognition and the antagonism of this interaction by tamoxifen." *Cell* 95(7): 927-37.

Shiau, A. K., P. Coward, et al. (2001). "Orphan nuclear receptors: from new ligand discovery technologies to novel signaling pathways." *Curr Opin Drug Discov Devel* 4(5): 575-90.

Sladek, R., J. A. Bader, et al. (1997). "The orphan nuclear receptor estrogen-related receptor alpha is a transcriptional regulator of the human medium-chain acyl coenzyme A dehydrogenase gene." *Mol Cell Biol* 17(9): 5400-9.

Smith, A. G. and G. E. Muscat (2005). "Skeletal muscle and nuclear hormone receptors: implications for cardiovascular and metabolic disease." *Int J Biochem Cell Biol* 37(10): 2047-63.

Suetsugi, M., L. Su, et al. (2003). "Flavone and isoflavone phytoestrogens are agonists of estrogen-related receptors." *Mol Cancer Res* 1(13): 981-91.

Vanacker, J. M., K. Pettersson, et al. (1999). "Transcriptional targets shared by estrogen receptor-related receptors (ERRs) and estrogen receptor (ER) alpha, but not by ERbeta." *Embo J* 18(15): 4270-9.

Wende, A. R., J. M. Huss, et al. (2005). "PGC-1alpha coactivates PDK4 gene expression via the orphan nuclear receptor ERRalpha: a mechanism for transcriptional control of muscle glucose metabolism." *Mol Cell Biol* 25(24): 10684-94.

Willy, P. J. et al. (1997). "Unique requirements for retinoid-dependent transcriptional activation by the orphan receptor LXR." *Genes Dev* 11(3) 289-98.

Willy, P. J., I. R. Murray, et al. (2004). "Regulation of PPAR-gamma coactivator 1alpha (PGC-1alpha) signaling by an estrogen-related receptor alpha (ERRalpha) ligand." *Proc Natl Acad Sci USA* 101(24): 8912-7.

Zhang, Z. and C. T. Teng (2000). "Estrogen receptor-related receptor alpha 1 interacts with coactivator and constitutively activates the estrogen response elements of the human lactoferrin gene." *J Biol Chem* 275(27): 20837-46.

Zorzato, F., E. Scutari, et al. (1993). "Chlorocresol: an activator of ryanodine receptor-mediated Ca2+ release." *Mol Pharmacol* 44(6): 1192-201.

Zuercher, W. J., S. Gaillard, et al. (2005). "Identification and structure-activity relationship of phenolic acyl hydrazones as selective agonists for the estrogen-related orphan nuclear receptors ERRbeta and ERRgamma." *J Med Chem* 48(9): 3107-9.

LENGTHY TABLES

The patent contains a lengthy table section. A copy of the table is available in electronic form from the USPTO web site (http://seqdata.uspto.gov/?pageRequest=docDetail&DocID=US07655756B2). An electronic copy of the table will also be available from the USPTO upon request and payment of the fee set forth in 37 CFR 1.19(b)(3).

What is claimed is:

1. A peptide fragment complex comprising an isolated ligand binding domain of human estrogen-related receptor gamma (ERRγ) consisting essentially of SEQ ID NO: 2 in complex with Bisphenol A.

2. A crystallized peptide fragment complex according to claim 1, wherein the crystallized peptide fragment complex has unit cell dimensions a=b=64.07 Å and c=136.48 Å, and space group $P4_12_12$.

* * * * *

```
                          SEQUENCE LISTING

<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
 1               5

<210> SEQ ID NO 2
<211> LENGTH: 222
<212> TYPE: PRT
<213> ORGANISM: Homo sapiens

<400> SEQUENCE: 2

Asn Lys Ile Val Ser His Leu Leu Val Ala Glu Pro Glu Lys Ile Tyr
 1               5                  10                  15

Ala Met Pro Asp Pro Thr Val Pro Asp Ser Asp Ile Lys Ala Leu Thr
            20                  25                  30

Thr Leu Cys Asp Leu Ala Asp Arg Glu Leu Val Val Ile Ile Gly Trp
        35                  40                  45
```

-continued

```
Ala Lys His Ile Pro Gly Phe Ser Thr Leu Ser Leu Ala Asp Gln Met
 50                  55                  60

Ser Leu Leu Gln Ser Ala Trp Met Glu Ile Leu Ile Leu Gly Val Val
 65                  70                  75                  80

Tyr Arg Ser Leu Ser Phe Glu Asp Glu Leu Val Tyr Ala Asp Asp Tyr
                 85                  90                  95

Ile Met Asp Glu Asp Gln Ser Lys Leu Ala Gly Leu Leu Asp Leu Asn
                100                 105                 110

Asn Ala Ile Leu Gln Leu Val Lys Lys Tyr Lys Ser Met Lys Leu Glu
                115                 120                 125

Lys Glu Glu Phe Val Thr Leu Lys Ala Ile Ala Leu Ala Asn Ser Asp
            130                 135                 140

Ser Met His Ile Glu Asp Val Glu Ala Val Gln Lys Leu Gln Asp Val
145                 150                 155                 160

Leu His Glu Ala Leu Gln Asp Tyr Glu Ala Gly Gln His Met Glu Asp
                    165                 170                 175

Pro Arg Arg Ala Gly Lys Met Leu Met Thr Leu Pro Leu Leu Arg Gln
                180                 185                 190

Thr Ser Thr Lys Ala Val Gln His Phe Tyr Asn Ile Lys Leu Glu Gly
            195                 200                 205

Lys Val Pro Met His Lys Leu Phe Leu Glu Met Leu Glu Ala
        210                 215                 220

<210> SEQ ID NO 3
<211> LENGTH: 223
<212> TYPE: PRT
<213> ORGANISM: Homo sapiens

<400> SEQUENCE: 3

Tyr Asn Lys Ile Val Ser His Leu Leu Val Ala Glu Pro Glu Lys Ile
  1               5                  10                  15

Tyr Ala Met Pro Asp Pro Thr Val Pro Asp Ser Asp Ile Lys Ala Leu
                 20                  25                  30

Thr Thr Leu Cys Asp Leu Ala Asp Arg Glu Leu Val Val Ile Ile Gly
             35                  40                  45

Trp Ala Lys His Ile Pro Gly Phe Ser Thr Leu Ser Leu Ala Asp Gln
 50                  55                  60

Met Ser Leu Leu Gln Ser Ala Trp Met Glu Ile Leu Ile Leu Gly Val
 65                  70                  75                  80

Val Tyr Arg Ser Leu Ser Phe Glu Asp Glu Leu Val Tyr Ala Asp Asp
                 85                  90                  95

Tyr Ile Met Asp Glu Asp Gln Ser Lys Leu Ala Gly Leu Leu Asp Leu
                100                 105                 110

Asn Asn Ala Ile Leu Gln Leu Val Lys Lys Tyr Lys Ser Met Lys Leu
            115                 120                 125

Glu Lys Glu Glu Phe Val Thr Leu Lys Ala Ile Ala Leu Ala Asn Ser
        130                 135                 140

Asp Ser Met His Ile Glu Asp Val Glu Ala Val Gln Lys Leu Gln Asp
145                 150                 155                 160

Val Leu His Glu Ala Leu Gln Asp Tyr Glu Ala Gly Gln His Met Glu
                    165                 170                 175

Asp Pro Arg Arg Ala Gly Lys Met Leu Met Thr Leu Pro Leu Leu Arg
                180                 185                 190

Gln Thr Ser Thr Lys Ala Val Gln His Phe Tyr Asn Ile Lys Leu Glu
```

-continued

```
                195                 200                 205
Gly Lys Val Pro Met His Lys Leu Phe Leu Glu Met Leu Glu Ala
    210                 215                 220

<210> SEQ ID NO 4
<211> LENGTH: 207
<212> TYPE: PRT
<213> ORGANISM: Homo sapiens

<400> SEQUENCE: 4

Asn Lys Ile Val Ser His Leu Leu Val Ala Glu Pro Glu Lys Ile Tyr
  1               5                  10                  15

Ala Met Pro Asp Pro Thr Val Pro Asp Ser Asp Ile Lys Ala Leu Thr
                 20                  25                  30

Thr Leu Cys Asp Leu Ala Asp Arg Glu Leu Val Val Ile Ile Gly Trp
             35                  40                  45

Ala Lys His Ile Pro Gly Phe Ser Thr Leu Ser Leu Ala Asp Gln Met
         50                  55                  60

Ser Leu Leu Gln Ser Ala Trp Met Glu Ile Leu Ile Leu Gly Val Val
 65                  70                  75                  80

Tyr Arg Ser Leu Ser Phe Glu Asp Glu Leu Val Tyr Ala Asp Asp Tyr
                 85                  90                  95

Ile Met Asp Glu Asp Gln Ser Lys Leu Ala Gly Leu Leu Asp Leu Asn
            100                 105                 110

Asn Ala Ile Leu Gln Leu Val Lys Lys Tyr Lys Ser Met Lys Leu Glu
            115                 120                 125

Lys Glu Glu Phe Val Thr Leu Lys Ala Ile Ala Leu Ala Asn Ser Asp
        130                 135                 140

Ser Met His Ile Glu Asp Val Glu Ala Val Gln Lys Leu Gln Asp Val
145                 150                 155                 160

Leu His Glu Ala Leu Gln Asp Tyr Glu Ala Gly Gln His Met Glu Asp
                165                 170                 175

Pro Arg Arg Ala Gly Lys Met Leu Met Thr Leu Pro Leu Leu Arg Gln
            180                 185                 190

Thr Ser Thr Lys Ala Val Gln His Phe Tyr Asn Ile Lys Leu Glu
        195                 200                 205
```